US008901167B2

(12) United States Patent
Nick et al.

(10) Patent No.: US 8,901,167 B2
(45) Date of Patent: Dec. 2, 2014

(54) PRODUCT AND PROCESS FOR INHIBITION OF BIOFILM DEVELOPMENT

(71) Applicant: National Jewish Health, Denver, CO (US)

(72) Inventors: Jerry A. Nick, Denver, CO (US); Travis S. Walker, Denver, CO (US); G. Scott Worthen, Denver, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 13/650,525

(22) Filed: Oct. 12, 2012

(65) Prior Publication Data
US 2013/0224200 A1 Aug. 29, 2013

Related U.S. Application Data

(63) Continuation of application No. 12/115,880, filed on May 6, 2008, now abandoned, which is a continuation of application No. 11/197,897, filed on Aug. 4, 2005, now abandoned.

(60) Provisional application No. 60/599,495, filed on Aug. 6, 2004.

(51) Int. Cl.
| *A01N 43/16* | (2006.01) |
| *A01N 43/30* | (2006.01) |
| *A01N 43/78* | (2006.01) |
| *A01N 43/02* | (2006.01) |
| *A61K 38/00* | (2006.01) |
| *A01N 57/00* | (2006.01) |
| *A61K 39/395* | (2006.01) |
| *A61K 31/522* | (2006.01) |
| *A61K 31/7072* | (2006.01) |
| *A61K 31/7076* | (2006.01) |
| *A61L 29/16* | (2006.01) |
| *A61L 15/44* | (2006.01) |
| *A61K 45/06* | (2006.01) |
| *A61K 9/00* | (2006.01) |

(52) U.S. Cl.
CPC ............ *A61K 39/395* (2013.01); *A61K 31/522* (2013.01); *A61K 31/7072* (2013.01); *A61K 31/7076* (2013.01); *A61L 29/16* (2013.01); *A61L 15/44* (2013.01); *A61K 45/06* (2013.01); *A61K 38/00* (2013.01); *A61K 9/007* (2013.01); *A61L 2300/432* (2013.01)
USPC ........... 514/456; 514/464; 514/369; 514/450; 514/9.4; 514/79; 514/101

(58) Field of Classification Search
CPC . A61K 45/06; A61K 2300/00; A61K 31/427; A61K 31/665; A61K 31/7036; A61K 31/19; A61K 31/22; A61K 31/327; A61K 31/341; A61K 31/343; A61K 31/357; A61K 31/381; A61K 31/402; A61K 31/426; A61K 38/00; A61K 31/522; A61K 31/7072; A61K 31/7076; A61K 39/395; A61K 9/007; A61K 38/02; A61K 38/57; A61K 31/785; A61K 38/12; A61K 38/50; A61K 47/481
See application file for complete search history.

(56) References Cited

U.S. PATENT DOCUMENTS

| 5,260,224 | A | 11/1993 | Stossel et al. |
| 5,312,813 | A | 5/1994 | Costerton et al. |
| 5,462,644 | A | 10/1995 | Woodson |
| 5,464,817 | A | 11/1995 | Stossel et al. |
| 5,981,568 | A | 11/1999 | Kunz et al. |
| 6,143,037 | A | 11/2000 | Goldstein et al. |
| 6,586,425 | B2 | 7/2003 | Kaufman et al. |
| 6,759,040 | B1 * | 7/2004 | Manyak et al. ............. 424/94.2 |
| 7,144,992 | B2 | 12/2006 | Madhyastha |
| 2002/0099438 | A1 | 7/2002 | Furst |
| 2003/0109837 | A1 * | 6/2003 | McBride-Sakal ............. 604/267 |
| 2003/0113742 | A1 | 6/2003 | Whiteley et al. |
| 2005/0008671 | A1 * | 1/2005 | Van Antwerp ................ 424/423 |
| 2006/0002889 | A1 | 1/2006 | Fitzpatrick |
| 2006/0030539 | A1 | 2/2006 | Nick et al. |
| 2006/0140911 | A1 * | 6/2006 | Sharp et al. .................. 424/93.6 |
| 2006/0239940 | A1 | 10/2006 | Nakayama et al. |
| 2007/0003538 | A1 | 1/2007 | Madhyastha |
| 2008/0199509 | A1 | 8/2008 | Nick et al. |
| 2008/0207556 | A1 | 8/2008 | Nick et al. |

FOREIGN PATENT DOCUMENTS

| WO | WO 02/083167 | 10/2002 |
| WO | WO 03/088914 | 10/2003 |
| WO | WO 2005/094579 | 10/2005 |

OTHER PUBLICATIONS

Farb et al. 1999. Circulation. 99:44-52.*
Bertrand et al. 2000. Circulation 102:624-629.*

(Continued)

*Primary Examiner* — Shulamith H Shafer
(74) *Attorney, Agent, or Firm* — Sheridan Ross P.C.

(57) ABSTRACT

Disclosed are compositions and methods for the inhibition of biofilm formation or reduction of existing or developing biofilms in a patient. These methods also inhibit the aggregation of bacteria that form biofilms in the airways. The methods include administering to a subject that has or is at risk of developing biofilms a compound or formulation that inhibits the formation or polymerization of actin microfilaments or depolymerizes actin microfilaments at or proximal to the site of biofilm formation. Such a compound can be administered in combination with a compound or formulation that inhibits the accumulation or activity of cells that are likely to undergo necrosis at or proximal to the site of biofilm formation (i.e., neutrophils). The methods and compositions can further include the use of anti-DNA and/or anti-mucin compounds, as well as other therapeutic compounds and compositions.

20 Claims, 15 Drawing Sheets

(56) References Cited

OTHER PUBLICATIONS

Balfour-Lynn "The protease-antiprotease battle in the cystic fibrosis lung," Journal of the Royal Society of Medicine, 1999, vol. 92, No. 37 Supplement, pp. 23-30.

Barnett "The rationale for the daily use of an antimicrobial mouthrinse," JADA, Nov. 2006, vol. 137, pp. 16S-21S.

Bleazard "The Role of Oxygen and The Interaction of Human Neutrophils with Viable Planktonic and Biofilm *Pseudomonas aeruginosa*," Montana State University, available at www.erc.montana.edu/Res-Lib99-SW/pubs/Theses/2001/Thesis01_Bleazard.htm., Jul. 2001, pp. 1-2.

Boucher "An Overview of the Pathogens of Cystic Fibrosis Lung Disease," Advanced Drug Delivery Reviews, Dec. 2002, vol. 54, No. 11, pp. 1359-1371.

Camenzind et al. "Local Vascular Therapy Against Thrombus and Proliferation: Clinical Trials Update," American College of Cardiology, 47th Annual Scientific Session, available at www.medscape.com/viewarticle/428985, printed Apr. 26, 2007, pp. 1-3.

Clark "The Commonality of Cutaneous Wound Repair and Lung Injury," Chest, Mar. 1991, vol. 99, No. 3, Supplement, pp. 57S-60S.

Cooper "Effects of Cytochalasin and Phalloidin on Actin," The Journal of Cell Biology, Oct. 1987, vol. 105, pp. 1473-1478.

Donlan "Biofilms and Device-Associated Infections," Emerging Infectious Diseases, Mar.-Apr. 2001, vol. 7, No. 2, pp. 277-281.

Egerbacher et al., "Ciprofloxacin causes cytoskeletal changes and detachment of human and rat chodrocytes in vitro", Archives of Toxicology, Jan. 2000, vol. 73, No. 10-11, pp. 557-563.

Gong et al. "Salivary Film Expresses a Complex Macromolecular Binding Site for *Streptococcus sanguis*," The Journal of Biological Chemistry, Mar. 24, 2000, vol. 275, No. 12, pp. 8970-8974.

Hagemann "Cystic Fibrosis Drug Therapy," Journal of Pediatric Health Care, May/Jun. 1996, vol. 10, pp. 127-134.

Halmerbauer et al. "The relationship of eosinophil granule proteins to ions in the sputum of patients with cystic fibrosis," Clinical and Experimental Allergy, Dec. 2000, vol. 30, No. 12, pp. 1771-1776.

Høiby "Understanding bacterial biofilms in patients with cystic fibrosis: current and innovative approaches to potential therapies," Journal of Cystic Fibrosis, Jan. 1, 2002, vol. 1, pp. 249-254.

Jackson et al. "The Role of Biofilms in Airway Disease," Seminars in Respiratory and Critical Care Medicine, 2003, vol. 24. No. 6, pp. 663-670.

Jaffé et al. "Anti-Inflammatory Effects of Macrolides in Lung Disease." Pediatric Pulmonary, Jun. 2001, vol. 31, No. 6, pp. 464-473.

Jansen et al. "Prevention of biofilm formation by polymer modification," Journal of Industrial Microbiology, Oct. 1995, vol. 15, No. 4, pp. 391-396.

Jensen et al. "Colistin inhalation therapy in cystic fibrosis patients with chronic *Pseudomonas aeruginosa* lung infection," Journal of Antimicrobial Chemotherapy, Jan. 1987, vol. 19, No. 6, pp. 831-838.

Jesaitis et al. "Compromised Host Defense on *Pseudomonas aeruginosa* Biofilms: Characterization of Neutrophil and Biofilm Interactions," The Journal of Immunology, Jan. 1, 2003, vol. 171, pp. 4329-4339.

Khardori et al. "Biofilms in Device-related infections," Journal of Industrial Microbiology, Sep. 1995, vol. 15, No. 3, pp. 141-147.

Kobayashi "Clinical role of autoantibody against bactericidal/permeability-increasing protein in chronic airway infection." Journal of Infection and Chemotherapy, Jun. 1998, vol. 4, No. 2, pp. 83-93.

Konstan et al. "Effect of High-Dose Ibuprofen in Patients with Cystic Fibrosis," The New England Journal of Medicine, Mar. 30, 1995, vol. 332, pp. 848-854.

Kubanek et al. "Seaweed resistance to microbial attack: a targeted chemical defense against marine fungi," PNAS, Jun. 10, 2003, vol. 100, No. 13, pp. 6916-6921.

Lethem et al. "The Origin of DNA Associated With Mucus Glycoproteins in Cystic Fibrosis Sputum." The European Respiratory Journal : Official Journal of the European Society for Clinical Respiratory Physiology, 1990, vol. 3, pp. 19-23.

Musk et al. "Chemical Countermeasures for the Control of Bacterial Biofilms: Effective Compounds and Promising Targets," Current Medicinal Chemistry, Aug. 1, 2006, vol. 13, No. 18, pp. 2163-2177.

Nemoto et al. "Effect of Varidase (Streptodornase) on Biofilm Formed by *Pseudomonas aeruginosa*." Chemotherapy, 2003, vol. 49, No. 3, pp. 121-125.

Olsson et al. "Arginie-Rich Cationic Proteins of Human Eosinophil Granules," Laboratory Investigation; A Journal of Technical Methods and Pathology, 1977, vol. 36, No. 5, pp. 493-500.

Parks et al. "Neutrophil enhancement of *Pseudomonas aeruginosa* biofilm development," J. Med. Microbiol., Apr. 2009, vol. 58, Part 4, pp. 492-502.

Perks et al. "DNA and Actin Bind and Inhibit Interleukin-8 Function in Cystic Fibrosis Sputa," American Journal of Respiratory and Critical Care Medicine, 2000, vol. 162, pp. 1767-1772.

Rowe et al. "Mechanisms of Disease: Cystic Fibrosis," The New England Journal of Medicine, May 12, 2005, vol. 352, pp. 1992-2001.

Schultz "Macrolide activities beyond their antimicrobial effects: macrolides in diffues panbronchiolitis and cystic fibrosis," Journal of Antimicrobial Chemotherapy, 2004, vol. 54, No. 1, pp. 21-28.

Schwab et al. "Role of Actin Filament Network in Burkholderia Multivorans Invasion in Well-Differentiated Human Airway Epithelia." Infection and Immunity, Nov. 2003, vol. 71, No. 11, pp. 6607-6609.

Sheils et al. "Actin Filaments Mediate DNA Fiber Formation in Chronic Inflammatory Airway Disease." American Journal of Pathology, Mar. 1996, vol. 148, No. 3, pp. 919-927.

Singh et al. "A component of innate immunity prevents bacterial biofilm development," Nature, May 30, 2002, vol. 417, No. 6888, pp. 552-555.

Smith et al., "Action of Cytochalasin B on Cultured Human Lymphocytes" Nature, Dec. 1967, vol. 16, No. 216, pp. 1134-1135.

Spooner et al. "Effects of Cytochalasin B upon Microfilaments Involved in Morphogenesis of Salivary Epithelium," Proceedings of the National Academy of Sciences, Jun. 1970, vol. 66, No. 2, pp. 360-364.

Stossel "Gesolin: Another Potential Therapy for CF Sputum!" available at www.cfri.org/news/94fall/res394f.html, Fall 1994, date of download Nov. 20, 2006, pp. 1-2.

Takeoka et al. "The In Vitro Effect of Macrolides on the Interaction of Human Polymorphonuclear Leukocytes With *Pseudomonas aeruginosa* in Biofilm," Chemotherapy, Jan. 1, 1998, vol. 44, No. 3, pp. 190-197.

Tamaoki "The Effects of Macrolides on Inflammatory Cells," Chest Journal, Feb. 2004, vol. 125, No. 2, pp. 41S-51S.

Tang et al. "Anionic poly (amino acid)s dissolve F-actin and DNA bundles, enhance DNase activity, and reduce the viscosity of cystic fibrosis sputum," American Journal of Physiology-Lung Cellular and Molecular Physiology, Jun. 17, 2005, vol. 289, pp. 599-605.

U.S. Preventive Services Task Force, "Aspirin for the Primary Prevention of Cardiovascular Events: Recommendation and Rationale," Annals of Internal Medicine, Jan. 15, 2002, vol. 136, No. 2, pp. 157-160.

Udagawa et al. "Cytochalasin E, an epoxide containing *Aspergillus*-derived fungal metabolite, inhibits angiogen," The Journal of Pharmacology and Experimental Therapeutics, Aug. 2000, vol. 294, No. 2, pp. 421-427.

Van Gameren et al., "Early complications of stenting in patients with congenital heart disease: a multicentre study," European Heart Journal, Nov. 2006, vol. 27, No. 22, pp. 2709-2715.

Vasconcellos et al. "Reduction in Viscosity of Cystic Fibrosis Sputum in Vitro by Gelsolin," Science, Feb. 18, 1994, vol. 263, No. 5149, pp. 964-971.

Walker et al. "Enhanced *Pseudomonas aeruginosa* biofilm development mediated by human neutrophils," Infection and Immunity, Jun. 2005, vol. 73, No. 6, pp. 3963-3701.

Weiner et al. "The Antimicrobial Activity of the Cathelicidin LL37 is Inhibited by F-actin Bundles and Restored by Gelsolin." Am. J Respir. Cell Mol. Biol., Dec. 2002, vol. 28, pp. 738-745.

(56) References Cited

OTHER PUBLICATIONS

Yasuda et al. "Interaction Between Biofilms Formed by *Pseudomonas aeruginosa* and Clarithromycin," Antimicrobial Agents and Chemotherapy, Sep. 1, 1993, vol. 37, No. 9, pp. 1749-1755.

Yoon et al. "*Pseudomonas aeruginosa* Anaerobic, Respiration in Biofilms: Relationships to Cystic Fibrosis Pathogenesis," Developmental Cell, Oct. 1, 2002, vol. 3, pp. 593-603.

Zahm et al. "Improved Activity of an Actin-Resistant DNase I Variant on the Cystic Fibrosis Airway Secretions," American Journal of Respiratory and Critical Care Medicine, Apr. 2001, vol. 163, No. 5, pp. 1153-1157.

Zhang et al. "Antimicrobial peptide therapeutics for cystic fibrosis," Antimicrobial Agents and Chemotherapy, Jul. 1, 2005, vol. 49, No. 7, pp. 2921-2927.

International Search Report for International (PCT) Patent Application No. PCT/US05/28076, mailed Oct. 2, 2007.

Written Opinion for International (PCT) Patent Application No. PCT/US05/28076, mailed Oct. 2, 2007.

International Preliminary Report on Patentability for International (PCT) Patent Application No. PCT/US05/28076, mailed Oct. 25, 2007.

Supplementary European Search Report for European Patent Application No. 05783370.9, dated Jun. 17, 2008.

\* cited by examiner

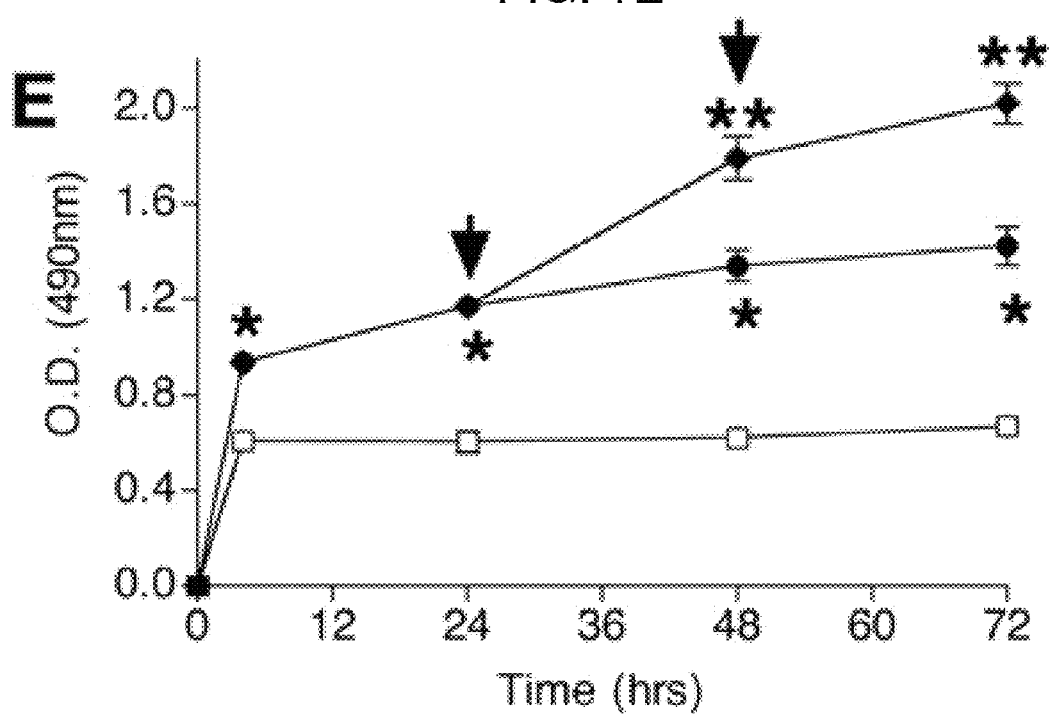

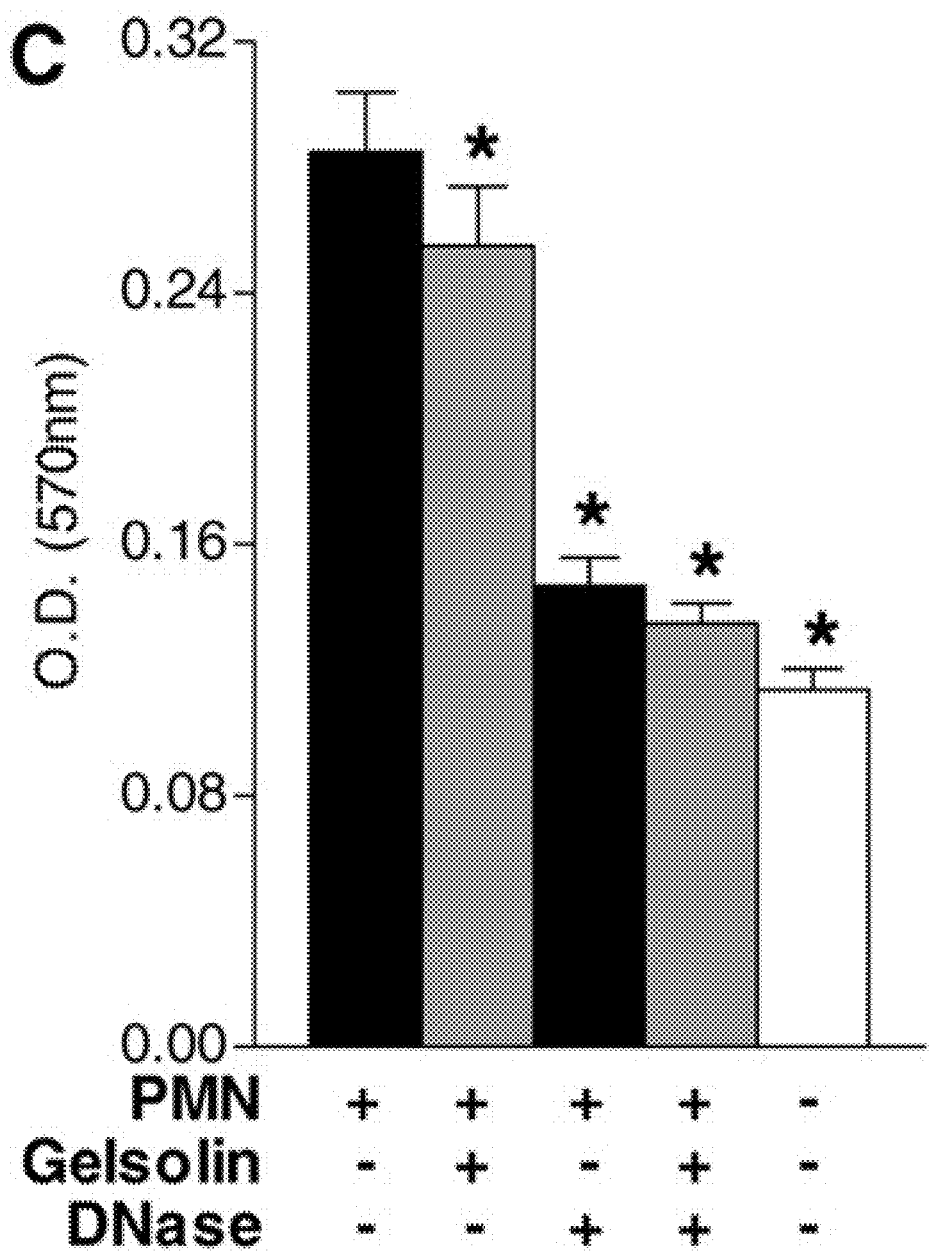

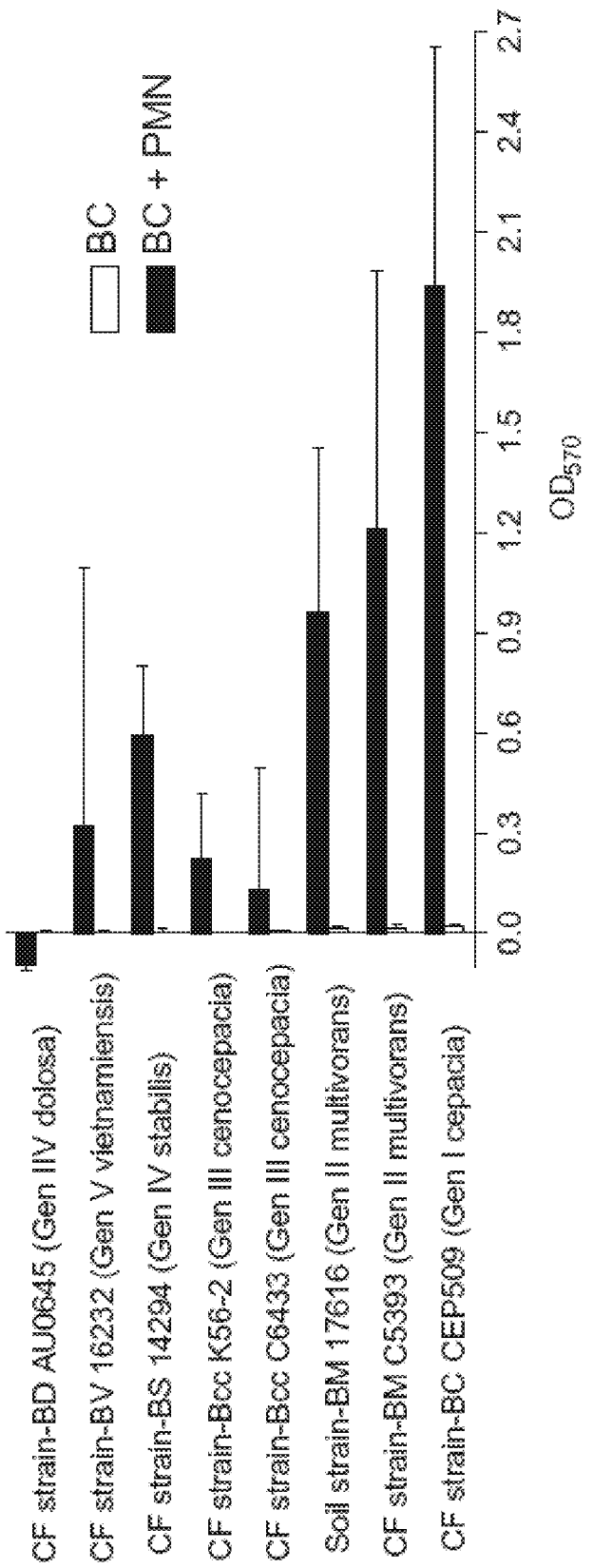

PRODUCT AND PROCESS FOR INHIBITION OF BIOFILM DEVELOPMENT

CROSS-REFERENCE TO RELATED APPLICATIONS

This application is a continuation of U.S. application Ser. No. 12/115,880, filed May 6, 2008, now abandoned, which claims the benefit to U.S. application Ser. No. 11/197,897, filed Aug. 4, 2005, now abandoned, which claims the benefit of priority under 35 U.S.C. §119(e) from U.S. Provisional Application No. 60/599,495, filed Aug. 6, 2004. The entire disclosure of each application is incorporated herein by reference in its entirety.

GOVERNMENT SUPPORT

This invention was supported, in part, using funds provided by NIH Grant Nos. HL061407 and HL068743, each awarded by the National Institutes of Health, and using funds provided by NIAID Grant No. AI15950, awarded by the National Institute of Allergy and Infectious Diseases. The government has certain rights to this invention.

FIELD OF THE INVENTION

The present invention generally relates to methods and compositions for the inhibition of biofilm formation or reduction of existing or developing biofilms in a patient.

BACKGROUND OF THE INVENTION

Cystic fibrosis (CF) lung disease features persistent neutrophil accumulation to the airways from the time of infancy (25). In the absence of detectable infection or endotoxin, bronchioalveolar lavage studies have recovered neutrophils ranging from $10^4$ to $10^6$ per ml from the airways of CF children (25, 29, 30). These children are frequently exposed to environmental strains of *P. aeruginosa*, but early infections can be transient, or be eradicated by aggressive antibiotic treatment and an exuberant host defense (6, 17, 35). Initial success in eradicating *P. aeruginosa* acquired from environmental sources likely occurs due to a low density of organisms, a lack of antibiotic resistance, and a generally nonmucoid phenotype. Eventually, persistent *P. aeruginosa* infection appears inevitable, and by adulthood, 80% of CF patients are chronically infected (16).

Factors that allow *P. aeruginosa* to become persistent are of particular interest, as chronic *P. aeruginosa* infection is clearly associated with increased morbidity and mortality in CF patients (13, 32, 37). The persistent *P. aeruginosa* infection is associated with numerous phenotypic and genetic changes by the bacteria within the CF airway (11, 14, 41) including the formation of biofilms (1, 11, 40). Bacterial biofilms are surface-attached communities of cells encased within a self-produced extracellular polysaccharide matrix. Biofilm development proceeds through a series of programmed steps including initial surface attachment, formation of three-dimensional microcolonies, and finally the development of a 'mature' biofilm (26). The detection of a specific pattern of quorum-sensing signaling molecules in the CF airway suggests that *P. aeruginosa* in the CF airway exists primarily in the biofilm form (40), and this conclusion is supported by the inability of antibiotics and host defense mechanisms to eradicate the infection (1, 11, 40).

Despite some promising advances, correction of CF by gene therapy is not yet attainable. Currently, antibiotic regimens coupled with drugs that facilitate the clearance of purulent airway secretions remain the mainstay treatments for progressive airway disease. Inhalation of purified rhDNase (Pulmozyme; Genentech, USA), which digests extracellular DNA present in the CF airway, is widely used as a respiratory decongestant. Such treatment is clinically effective for diminishing sputum viscosity and stabilizing the forced expiratory volume (FEV) (Fuchs et al., *N Engl J Med* 331:637-642, 1994).

In addition to CF, a variety of other medical conditions and treatments can cause the undesirable development of biofilms. For example, a variety of microbial infections can be characterized by biofilm formation, including, but not limited to, infectious kidney stones, cystitis, catheter-related infection (kidney, vascular, peritoneal), medical device-related infections, prostatitis, dental caries, chronic otitis media, bronchiectasis, bacterial endocarditis, Legionnaire's disease, orthopedic implant infection, osteomyelitis, wounds, acne, and biliary stents. Therefore, there is a need in the art for improved therapeutic approaches for the inhibition of biofilm formation and/or the reduction or elimination of biofilms, which will be useful for the treatment of conditions such as cystic fibrosis, as well as other diseases and conditions that are associated with the formation of microbial biofilms.

SUMMARY OF THE INVENTION

One embodiment of the present invention relates to a method to inhibit biofilm formation or reduce biofilms in a subject. The method includes the step of administering to a subject that has or is at risk of developing biofilms, a compound that inhibits the formation or polymerization of actin microfilaments or depolymerizes actin microfilaments at or proximal to the site of biofilm formation or the site of infection by a microorganism that forms biofilms. Typically, the actin microfilaments targeted by the present method are formed largely from the content of a cell that undergoes necrosis at or proximal to the site of biofilm formation or the site of infection by a microorganism that forms biofilms. Such cells include, but are not limited to, neutrophils, airway epithelial cells or other epithelial cells, macrophages, monocytes, lymphocytes, eosinophils, and the infectious microbe itself (e.g., *P. aeruginosa*).

Suitable compounds for use in this embodiment of the invention include, but are not limited to: cytochalasins, latrunculins, misakinolides, swinholides, myacolides, spinxolides, and scytophycins. Specific compounds which are useful in the present invention include, but are not limited to, cytochalasin B, cytochalasin D, latrunculin A, misakinolide A, swinholide A, myacolide B, spinxolide, scytophycin, domain 1 of gelsolin, destrin or profilin A further embodiment of the method of the present invention includes a step of administering to a subject a compound that inhibits accumulation of, inhibits necrosis of, or inhibits release of the cellular contents of, cells that undergo necrosis, at or proximal to the site of biofilm formation or the site of infection by a microorganism that forms biofilms. Such cells are described above. This step can be performed in combination with the administration of the anti-actin microfilament compound described above, or as an alternate method for inhibiting biofilm formation or reducing biofilms in a subject. For example, the compound preferably inhibits the adherence of, migration to, or the sensing or response to chemoattractants by neutrophils, or inhibits the activity or release of a cytokine, chemokine or chemoattractant that attracts or enhances neutrophil activity.

Suitable compounds for use in this embodiment of the invention include, but are not limited to: cytokine inhibitors, chemokine inhibitors, chemoattractant inhibitors, fluoroquinolones, Cox inhibitors, leukotiene receptor antagonists, leukotriene synthesis inhibitors, inhibitors of the p38 MAP kinase pathway, and glucocorticoids. More specifically, compounds that are useful in this embodiment of the invention include, but are not limited to: any inhibitor of eicosanoid synthesis and release, including any Cox-2 inhibitor; Cox-1 inhibitors; inhibitors of some certain prostaglandins (prostaglandin E(2); PGD(2)), inhibitors of certain leukotrienes ($LTB_4$); classes of antibiotics with known direct or indirect anti-inflammatory effects, including macrolides (e.g. azithromycin) and fluoroquinolones (e.g., levofloxacin; moxifloxacin; gatifloxacin); inhibitors of p38 MAP kinase; antagonists of growth factors which regulate neutrophil release, including granulocyte colony-stimulating factor (G-CSF) (e.g., antibodies or antigen binding fragments thereof, G-CSF antagonist variants or mimetics, drugs that antagonize the function of G-CSF); antagonists of granulocyte-macrophage colony-stimulating factor (GM-CSF); inhibitors of the function of cytokines and chemokines, including antagonists of tumor necrosis factor (TNF), antagonists of interleukin-8 (IL-8); transforming growth factor beta (TGF-beta); antibodies that block sites of neutrophil adhesion and thereby limit neutrophil accumulation to sites of inflammation, including anti-beta2 integrins (e.g., anti-CD11/CD18) and anti-ICAM-1; and neutrophil inhibitory material from other organisms, (e.g., excretory-secretory (ES) material from the parasitic nematode *Nippostrongylus brasiliensis*). A preferred compound is an anti-inflammatory compound.

In any of the above-described embodiments, the method can further include administering to the subject an anti-DNA compound and/or an anti-mucin compound. The method can also include administering to the subject a compound for treatment of a disease or condition associated with biofilm formation.

Preferably, the compound is administered when a disease or condition associated with biofilm formation is diagnosed or suspected. In one aspect, the compound is administered prior to the treatment of the subject with a process that may cause a biofilm to form in the patient. In one aspect, the compound is administered with a pharmaceutically acceptable carrier. In another aspect, the compound is administered directly to or proximal to the site of biofilm formation or potential therefore. In one aspect, the compound is administered to the lung or airways of the subject. In another aspect, the compound is applied to a prosthetic graft or administered to the subject receiving the graft prior to or during the implantation or utilization of the graft. In another aspect, the compound is applied to a catheter prior to or during use of the catheter by a subject. In another aspect, the compound is applied to the site of a wound or to the wound dressing when the wound is treated. In yet another aspect, the compound is applied to a medical device that contacts a subject tissue surface prior to or during use of the medical device by a subject.

The biofilms to be prevented, inhibited or treated may be caused by any condition or disease. For example, the biofilm may form in connection with a disease or condition in an organ, tissue or body system (e.g., lung, urinary tract, head and neck, vascular system, bone, skin, abdomen). Similarly, the biofilm may form on a surface of a tissue, organ or bodily part (e.g., lung, medium airways, ureter, urethra, bladder, prostate, mouth, ear, heart valve, vein, joint, bone, skin, and bile duct.). The biofilm may form in connection with a disease or condition selected from: infectious kidney stones, cystitis, catheter-related infection (kidney, vascular, peritoneal), medical device-related infections, prostatitis, dental caries, chronic otitis media, cystic fibrosis, bronchiectasis, bacterial endocarditis, Legionnaire's disease, orthopedic implant infection, osteomyelitis, wounds, acne, and biliary stents.

The microorganism responsible for biofilm formation includes, but is not limited to, *Pseudomonas aeruginosa, Burkholderia multivorans, Streptococcus sanguis, Escherichia coli,* and *Streptococcus viridans*.

Another embodiment of the present invention relates to a composition for inhibiting biofilm formation or reducing biofilms in a subject. The composition can comprise any one, two, three, four, five, or more compounds as described above. In one embodiment, the composition includes: (1) a first compound that inhibits the formation or polymerization of actin microfilaments or depolymerizes actin microfilaments at or proximal to the site of biofilm formation; and (2) a second compound that is an anti-DNA compound. This composition can further include a compound that inhibits the accumulation of, necrosis of, or release of the cellular contents of, neutrophils at or proximal to the site of biofilm formation, and a carrier suitable for application to the site of biofilm formation. In another aspect, the composition can include: (1) a first compound that inhibits the formation or polymerization of actin microfilaments or depolymerizes actin microfilaments at or proximal to the site of biofilm formation; and (2) a second compound that inhibits the accumulation of, necrosis of, or release of the cellular contents of, neutrophils at or proximal to the site of biofilm formation, and a carrier suitable for application to the site of biofilm formation.

Yet another embodiment of the present invention relates to a method to identify a compound that inhibits necrotic cell-enhanced biofilm formation or reduces necrotic cell-enhanced biofilms in a subject. The method includes the steps of: (a) contacting a putative inhibitory compound with a microbial culture in the presence and absence of a population of cells or a lysate thereof, wherein the microbial culture forms biofilms and is in a planktonic state prior to contact with the putative inhibitory compound, and wherein the population of cells undergoes necrosis in the presence of the microbial cells; and (b) measuring biofilm formation after contact with the putative regulatory compound as compared to in the absence of the compound and as compared to in the presence and absence of the population of cells or lysate thereof; wherein a decrease in biofilm formation in the presence of the putative regulatory compound and the presence of the population of cells or lysate thereof, as compared to in the absence of the population of cells or lysate thereof and as compared to in the absence of the putative regulatory compound, indicates that the putative regulatory compound inhibits necrotic cell-enhanced biofilm formation or reduces necrotic cell-enhanced biofilms. In one aspect, the population of cells is a population of neutrophils. Other aspects of this method can be expanded as described elsewhere herein.

BRIEF DESCRIPTION OF THE DRAWINGS OF THE INVENTION

FIG. 1E shows that exopolysaccharide staining of biofilm density demonstrated that the presence of neutrophils resulted in a greater quantity of biofilm compared to *P. aeruginosa* in the absence of neutrophils by 4 hrs (mean±SD of O.D. measurements (n=21). *p<0.05) (biofilm development of *P. aeruginosa* alone (□); biofilm development of *P. aeruginosa* in the presence of neutrophils (●); additional neutrophils added 24 and 48 hrs (arrows) after the initiation of the biofilm (♦)).

Figure 2A:
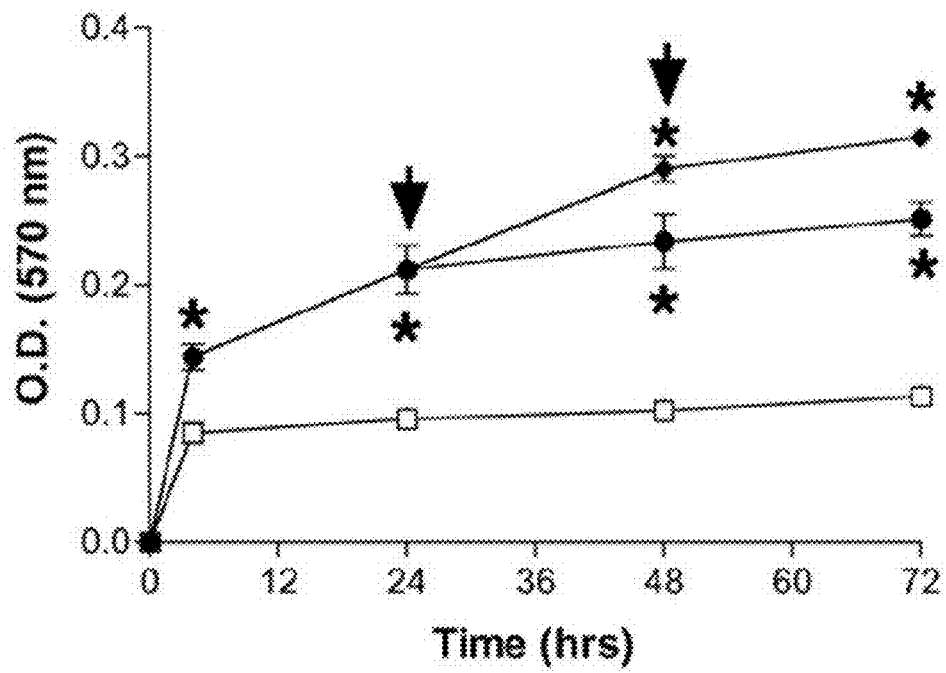

FIG. 2A shows that the presence of lysed neutrophils resulted in a greater quantity of biofilm compared to *P. aeruginosa* in the absence of neutrophils by 4 hrs (biofilm development of *P. aeruginosa* alone (□); biofilm development of *P. aeruginosa* in the presence of lysed neutrophils (●); additional lysed neutrophils added 24 and 48 hrs (arrows) after the initiation of the biofilm (♦)).

Figure 2B:
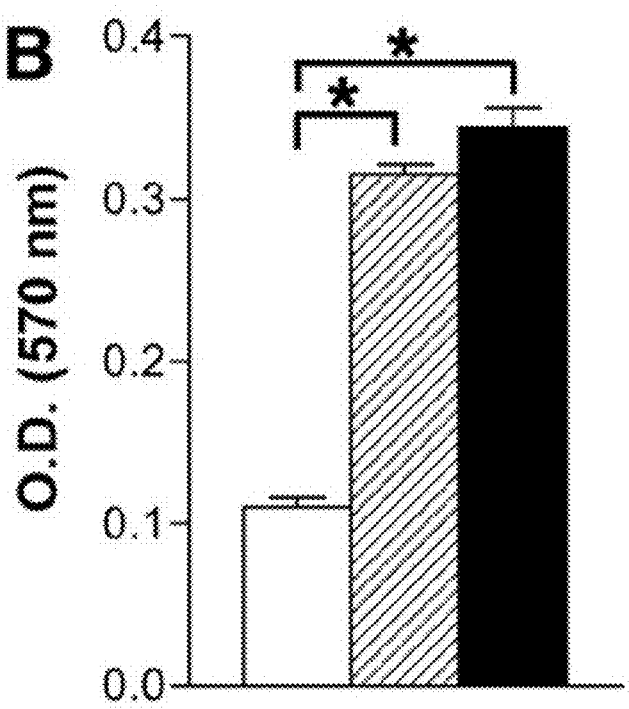

FIG. 2B shows that by 72 hrs, lysed neutrophils added at 0, 24, and 48 hrs (hatched bar) achieved 92% of the biofilm development seen with viable neutrophils added at 0, 24, and 48 hrs (solid bar) (open bar shows *P. aeruginosa* in the absence of neutrophils).

Figure 2C:
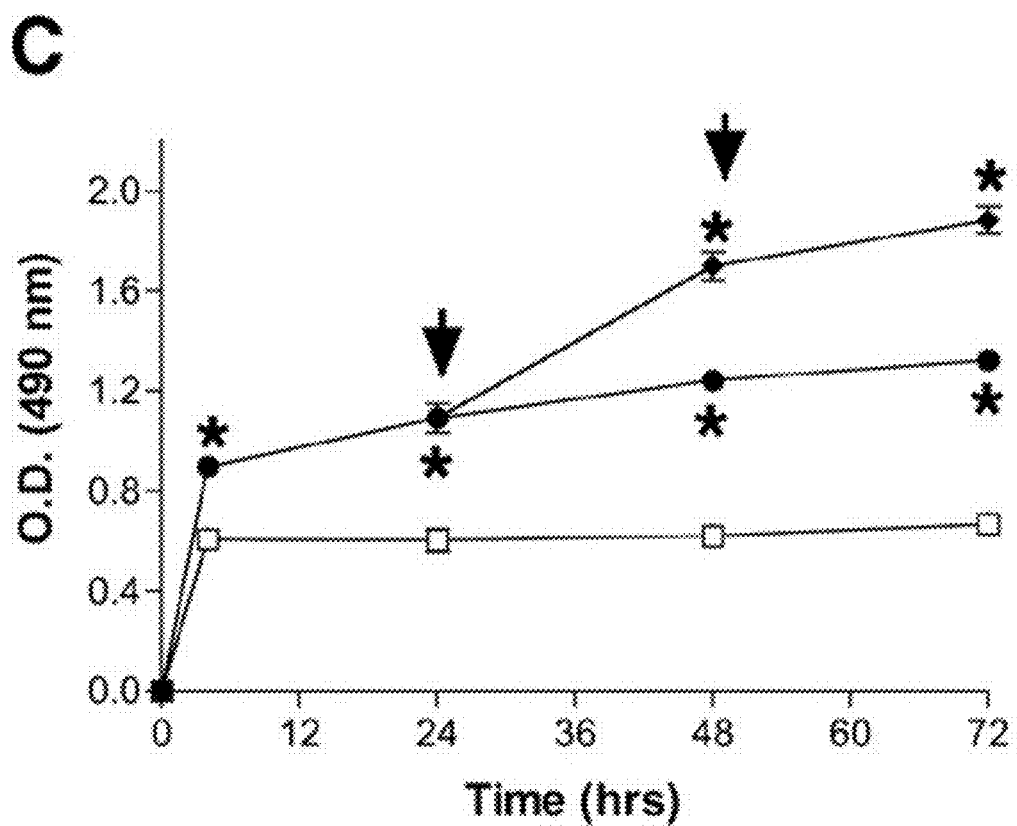

FIG. 2C shows that the presence of lysed neutrophils resulted in a greater quantity of biofilm compared to *P. aeruginosa* in the absence of neutrophils by 4 hrs (biofilm development of *P. aeruginosa* alone (□); biofilm development of *P. aeruginosa* in the presence of lysed neutrophils (●); additional lysed neutrophils added 24 and 48 hrs (arrows) after the initiation of the biofilm (♦)).

Figure 2D:
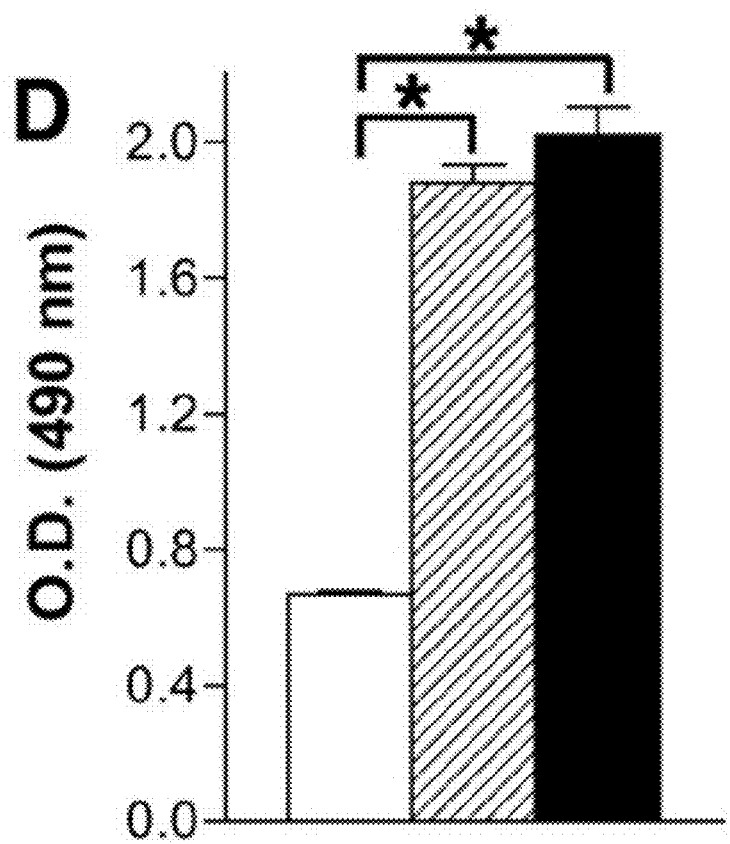

FIG. 2D shows that by 72 hrs, lysed neutrophils added at 0, 24, and 48 hrs (hatched bar) achieved 94% of the biofilm development seen with viable neutrophils added at 0, 24, and 48 hrs (solid bar) (open bar shows *P. aeruginosa* in the absence of neutrophils).

Figure 3A:
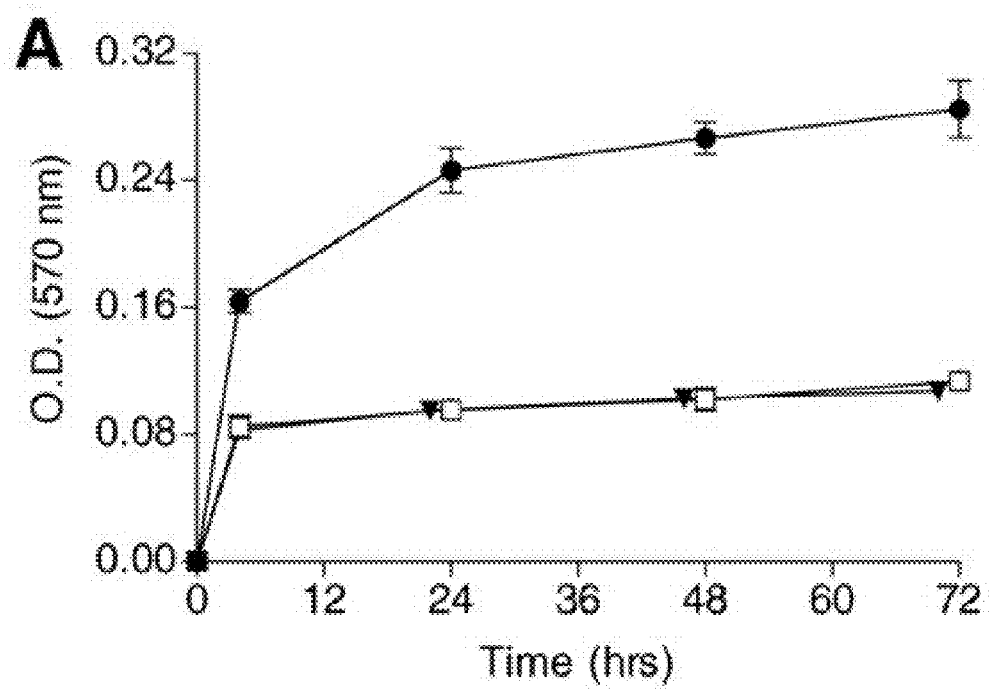

FIG. 3A shows that isolated neutrophil granule proteins failed to enhance the density of biofilm formation (*P. aeruginosa* (▼) was combined with granule proteins compared to *P. aeruginosa* (□) in the absence of granule proteins, and *P. aeruginosa* combined with live neutrophils (●)).

Figure 3B:
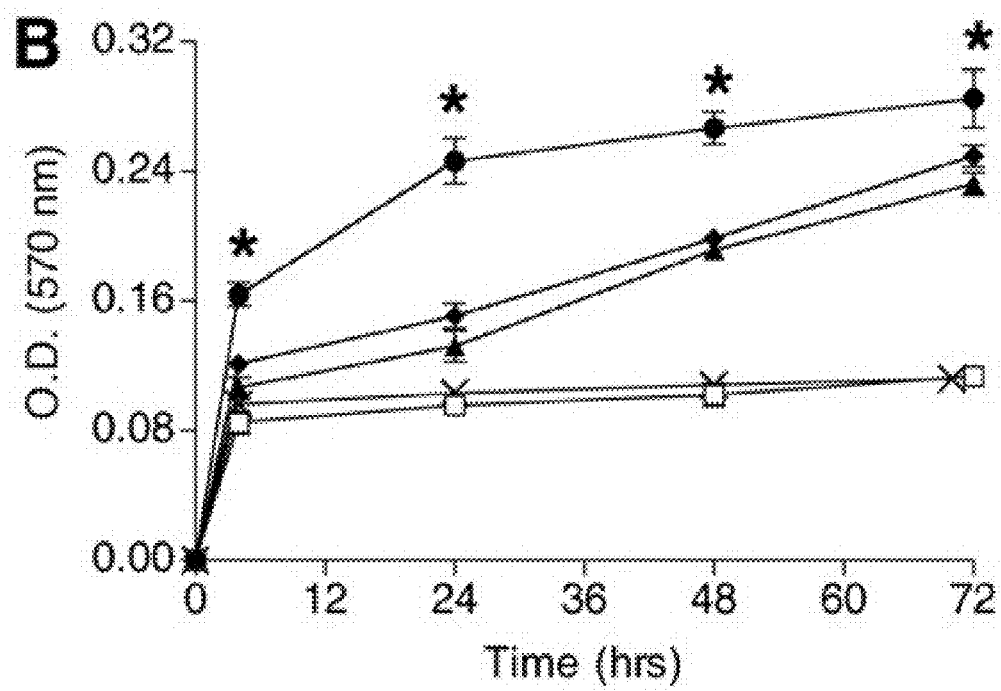

FIG. 3B shows that actin and DNA enhance *P. aeruginosa* biofilm development (biofilm development of *P. aeruginosa* alone (□); biofilm development of *P. aeruginosa* in the presence of live neutrophils (●); biofilm development of *P. aeruginosa* supplemented with purified globular monomeric actin (G-actin (▲); biofilm development of *P. aeruginosa* supplemented with purified neutrophil DNA alone (X); biofilm development of *P. aeruginosa* supplemented with both actin and neutrophil DNA (♦)).

FIG. 3C shows the loss of biofilm enhancement by disruption of DNA and actin (bars show neutrophil-induced enhancement of biofilm formation in the presence or absence of the compounds indicated under each bar).

Figure 4:
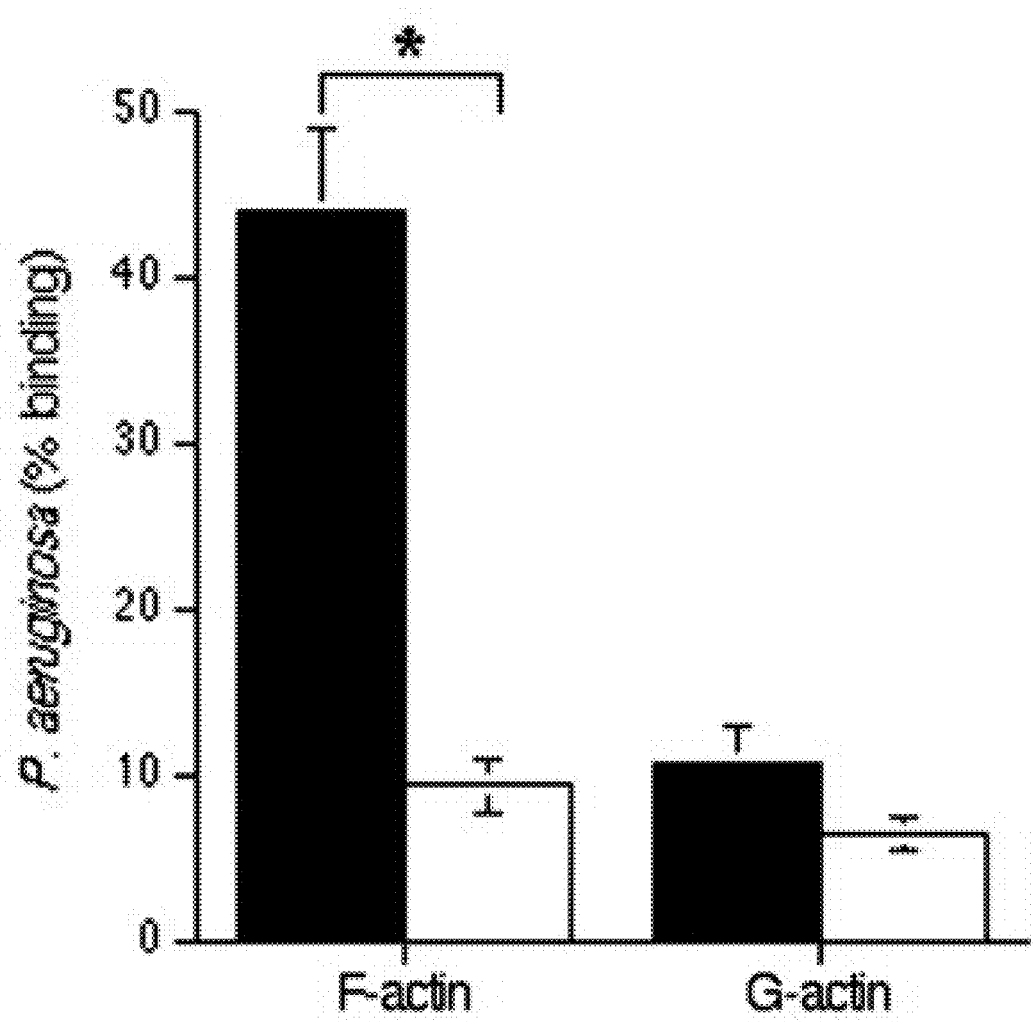

FIG. 4 shows actin binding by *P. aeruginosa*.

Figure 5:
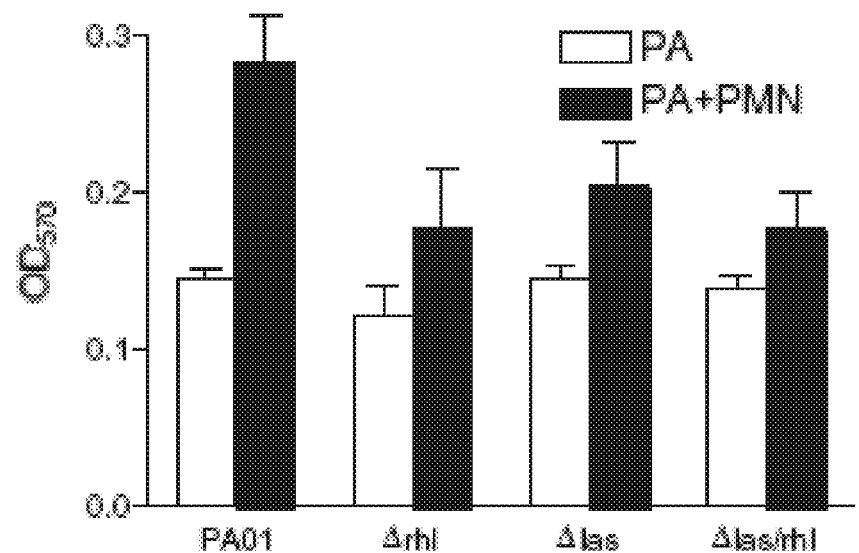

FIG. 5 shows that deletion of genes encoding the quorum-sensing signals rhl (ΔrhlR), las (ΔlasR) or both (ΔrhlR/lasR) resulted in little change in biofilm development in the absence of neutrophils, and that these mutant strains did not respond to neutrophils by developing a thicker biofilm.

Figure 6:
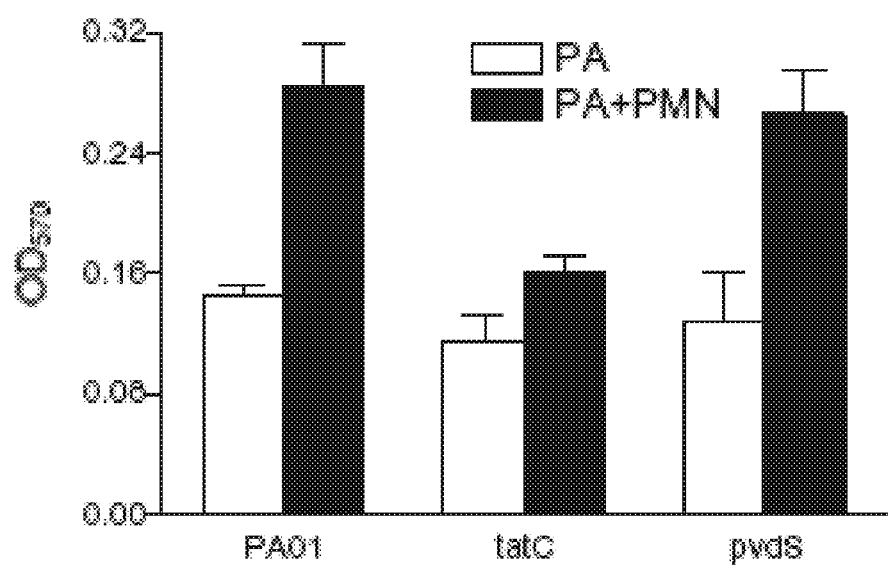

FIG. 6 shows that ΔpvdS strains formed biofilms equivalent to PA01 in the presence of neutrophils and that a ΔtatC mutant also forms biofilms poorly and was not effected by the presence of neutrophils.

Figure 7:
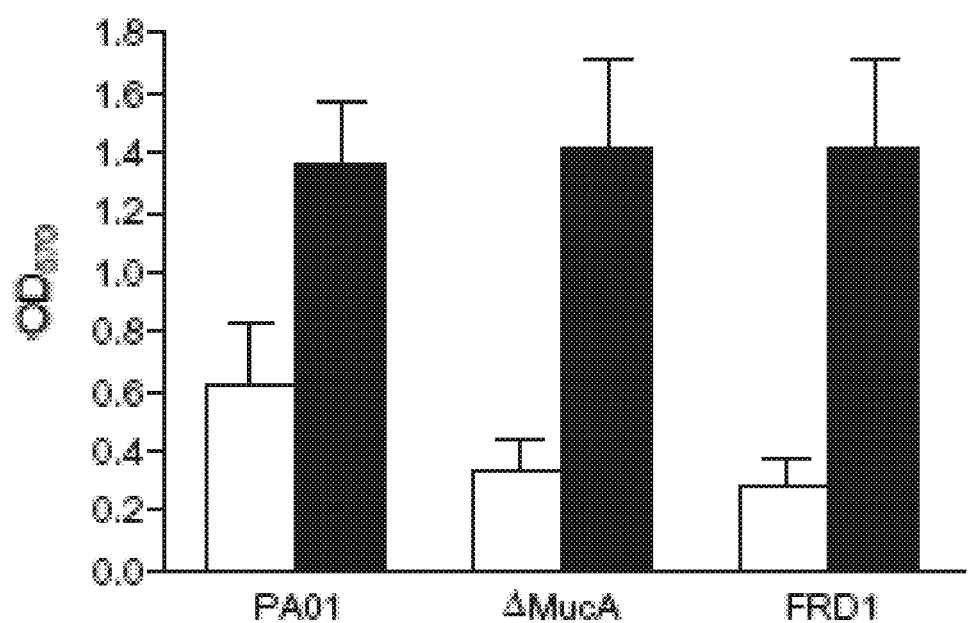

FIG. 7 shows that the ΔmucA mutant or the mucoid CF strain FDR1 demonstrate decreased biofilm development relative to PA01, but in the presence of neutrophils, this phenotype was no longer observed.

Figure 8:
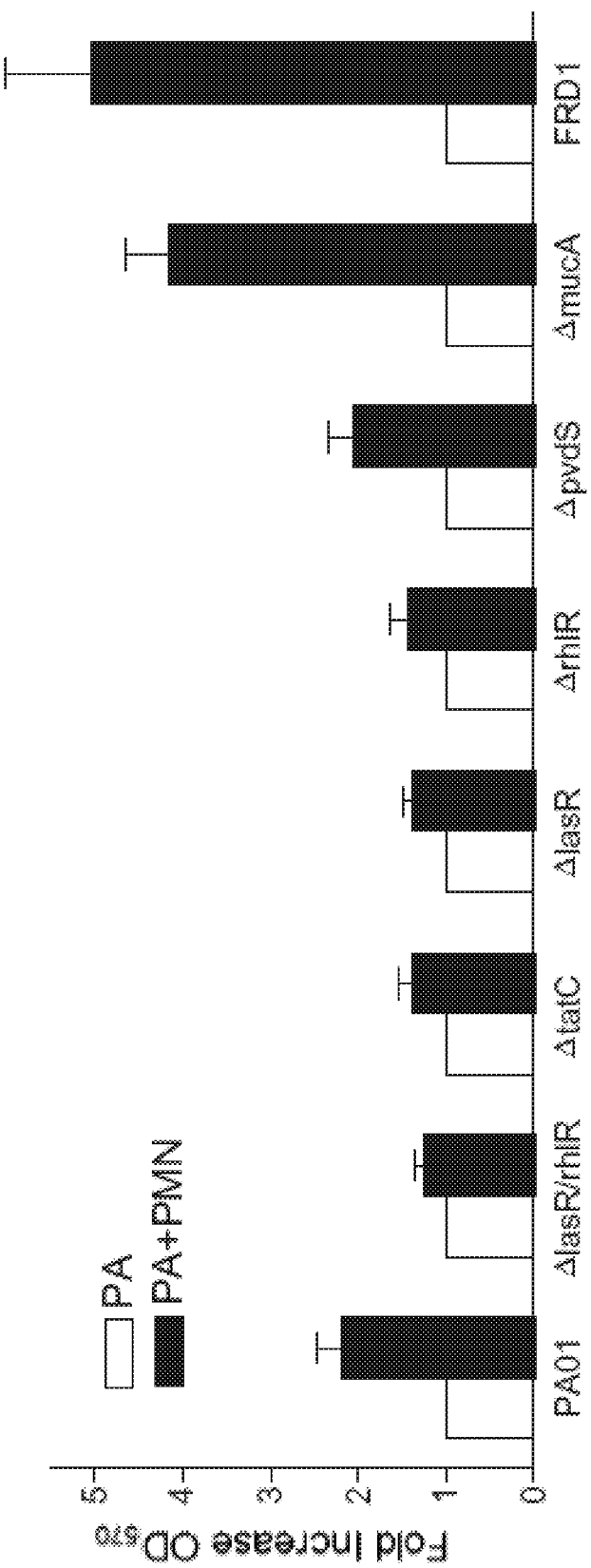

FIG. 8 show the index of neutrophils-enhancement of mutant strains, where the density of the biofilm in the presence of neutrophils is plotted as a fold-increase of the biofilm density relative to the strain in the absence of neutrophils.

Figure 9A:
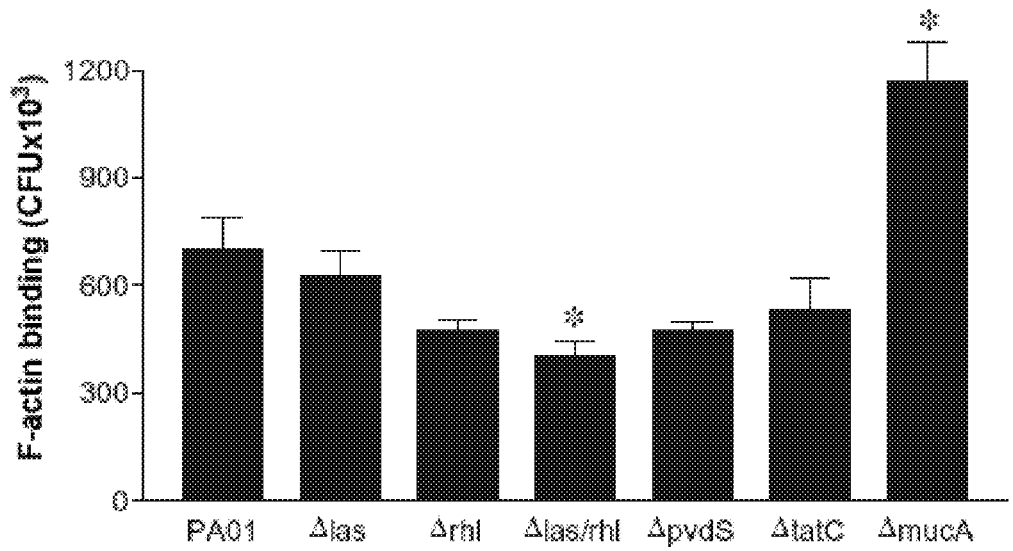

FIG. 9A shows that the deletion of genes encoding the quorum-sensing signals rhl (ΔrhlR), las (ΔlasR) or both (ΔrhlR/lasR) resulted in decreased binding to F-actin, while deletion of genes encoding for alginate results in increased F-actin binding.

Figure 9B:
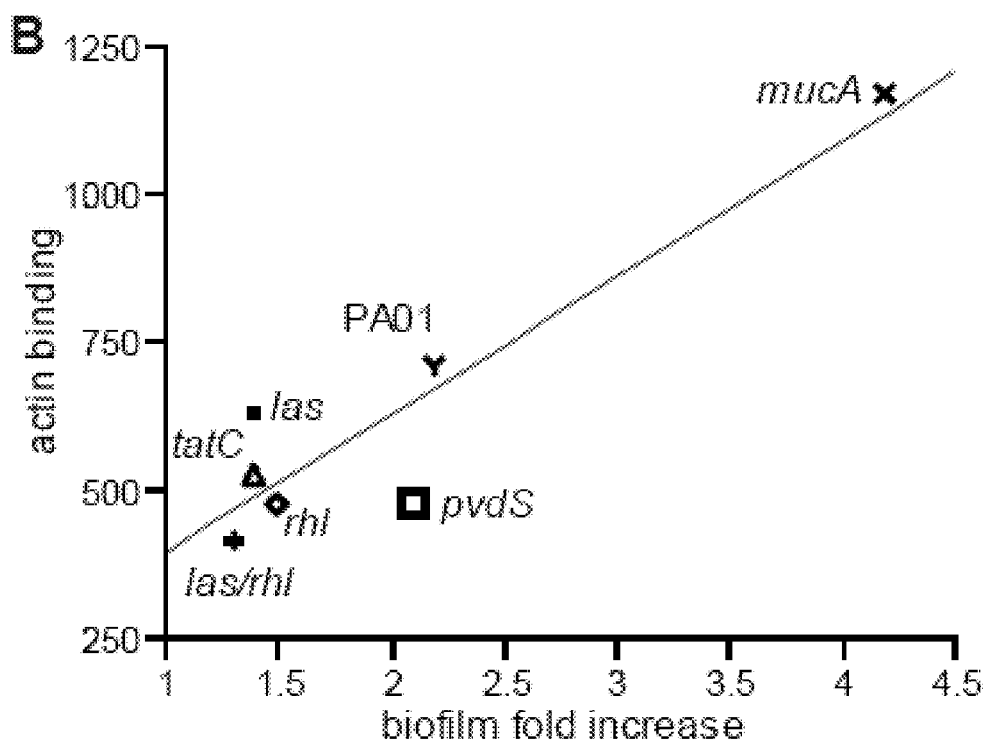

FIG. 9B shows that the extent of F-actin binding by PA01 and isogenic mutants significantly correlated with the neutrophil-induced fold-change of biofilm growth.

Figure 10:
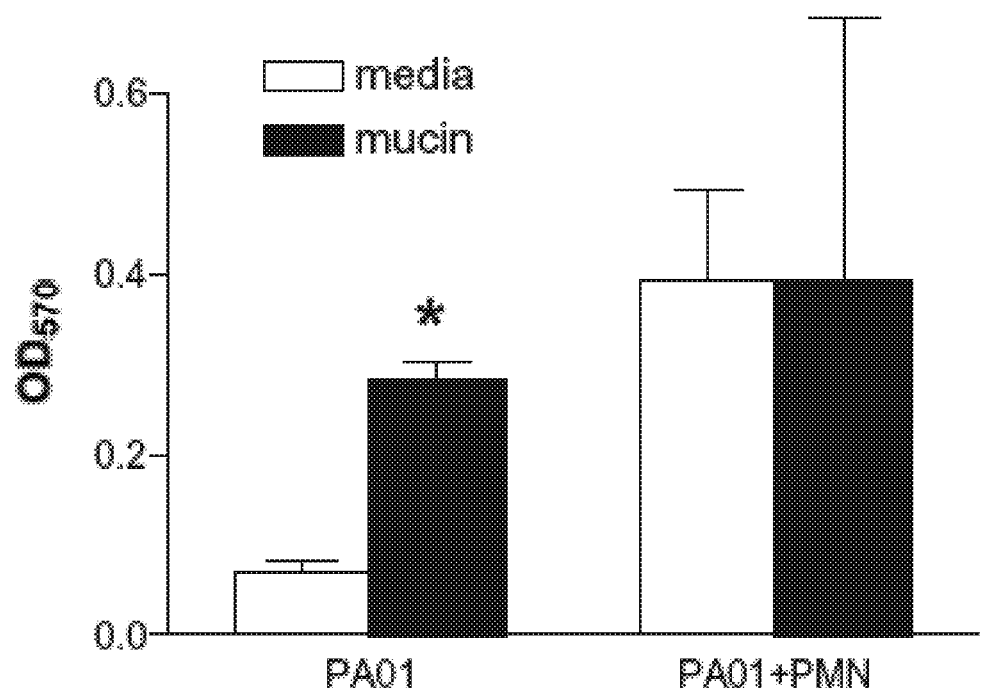

FIG. 10 shows the effect of mucin on *P. aeruginosa* biofilm development.

FIG. 11 shows the effect of neutrophils on Bcc biofilm formation.

DETAILED DESCRIPTION OF INVENTION

The present invention generally relates to a composition and method for the inhibition of biofilm formation or reduction of existing or developing biofilms in a patient. The methods of the present invention can also inhibit the aggregation of bacteria that form biofilms in the airways. In one embodiment, the method comprises administering to a patient that has or is at risk of developing biofilms a compound or formulation that inhibits the formation or polymerization of actin microfilaments or depolymerizes actin microfilaments at or proximal to the site of biofilm formation. In another, or additional, aspect, the method comprises administering to a patient that has or is at risk of developing biofilms a compound or formulation that inhibits (reduces, decreases, prevents) neutrophil accumulation or activity at or proximal to the site of biofilm formation. These aspects of the invention are based on the inventors' discovery that the presence of neutrophils at the site of bacterial infection enhances initial bacterial biofilm development in patients with cystic fibrosis through the formation of polymers of actin microfilaments and DNA from necrotic neutrophils. Therefore, inhibition of the neutrophil accumulation and therefore the subsequent polymerization of actin microfilaments and DNA at the site of infection will inhibit the formation and establishment of biofilms, providing a significant benefit to a patient. In addition, this discovery can be extended to other diseases and conditions associated with biofilm formation and particularly where neutrophils are involved in an inflammatory response to the disease or condition, and more particularly, when neutrophil association with an inflammatory process is chronic or prolonged.

Persistent neutrophil accumulation and necrosis in the CF airways results in sputum highly-enriched with DNA, actin, and granule proteins, which are all clearly implicated in the pathogenesis of CF lung disease (2, 25, 28, 33, 36, 38). Based on the concept that early CF lung disease features low numbers of planktonic, environmental strains of *P. aeruginosa* entering a neutrophil-rich airway (6), the present inventors tested the effect of neutrophils on the earliest stages of *P. aeruginosa* biofilm formation using a concentration of neutrophils compatible with the quantity of cells present in the airways of CF children prior to persistent *P. aeruginosa* infection, and concentrations of *P. aeruginosa* consistent with early infection (7, 29).

The present inventors have found that neutrophils enhance initial *P. aeruginosa* biofilm development through formation of a biological matrix comprised of actin and DNA polymers. These polymers are present in CF sputum, and disruption of the polymers dispersed associated *P. aeruginosa* and reduced biofilm development. Specifically, the biofilm enhancement coincides with a significant reduction of *P. aeruginosa* in the planktonic phase, resulting in little decrease in the overall number of viable bacteria after the first 4 hours of incubation. The mechanism of neutrophil biofilm enhancement was identified as being polymers comprised of actin and DNA. The bacteria bind to F-actin, and disruption of the polymers with DNase results in dispersion of the bacteria and a reduction in biofilm development. The presence of these actin/DNA polymers, with co-localization of *P. aeruginosa*, was confirmed in both neutrophil lysates and CF sputum. The introduction of additional neutrophils after 24 and 48 hours further enhanced *P. aeruginosa* biofilm development, while exposure to fewer neutrophils resulted in a lesser degree of biofilm enhancement (data not shown).

These findings demonstrate a potential maladaptation of the primary innate response, as cellular components from necrotic neutrophils can serve as a biological matrix to facilitate *P. aeruginosa* biofilm formation when eradication of infection fails. *P. aeruginosa* biofilm formation in the CF airways appears to occur in the context of stagnant mucous plugs which are lodged in the airway lumen, and are largely composed of dead and dying neutrophils (45, 46). The short lifespan of the neutrophil in the present inventors' study is consistent with neutrophil survival in the bloodstream and in other in vitro systems where typical survival is 6 to 18 hrs (12, 27). When neutrophils and *P. aeruginosa* are combined in vitro, neutrophil killing of planktonic *P. aeruginosa* is maximal at about 50 min (20), but subsequent necrosis of the leukocyte occurs rapidly, and over time the ability of the remaining viable neutrophils to ingest and kill *P. aeruginosa* is overshadowed by bacterial multiplication. In the presence of infection or pro-inflammatory stimuli, apoptosis is prevented or delayed, and cells may be viable up to 36 hours (12, 27). The concentration of neutrophils ($10^7$/ml) used in this analysis was based on BAL sampling of the airways of CF infants prior to persistent *P. aeruginosa* infection where neutrophil recovery ranged from $10^4$-$10^6$ per ml (25, 29, 30), with an estimated recovery rate of approximately 1-2% (10). An even broader range of quantity of *P. aeruginosa* has been isolated from CF children during early infection (7,29), and the inventors selected $10^6$ cfu/ml as a representative concentration.

In clinical settings that do not feature massive accumulation of neutrophils, various host products have been found in association with bacterial biofilms. Heterogeneous salivary films contain secretory IgA and α-amylase, which represent a binding sites for *Streptococcus sanguis* in the formation of dental plaques (19). Nearly all types of in-dwelling medical devices can become coated with host proteins, electrolytes and organic materials which appear to contribute to the presence of persistent infection (8). Uropathogenic strains of *E. coli* can form organized biofilm-like colonies within the cytoplasm of bladder cells during a phase of urinary tract infection (24), and clots comprised of fibrin and platelets facilitate *Streptococcus viridans* survival in endocarditis (23). However, the potential of an immune cell, integral to host defense, to increase formation of a bacterial biofilm has never been reported.

Without being bound by theory, since virtually every eukaryotic cell contains significant quantities of actin, it is possible that other necrotic cells, in addition to neutrophils, could enhance *P. aeruginosa* biofilm development. Therefore, the present invention is not limited to the inhibition of the accumulation of, necrosis of, or release of the cellular contents of, neutrophils, but rather is extended to other necrotic cells that are present at a site of a microbial infection. For example, in a severe skin burn *P. aeruginosa* could conceivably utilize actin and DNA from necrotic epithelial cells. Similarly, the present invention is not limited to the inhibition of biofilms associated with bacterial infection, as other microbes can also form biofilms (discussed below).

Recent reports have identified new mechanisms by which neutrophils successfully kill bacteria. Neutrophils actively generate "neutrophil extracellular traps" (NETs) that bind to *Staphylococcus aureus* and other bacteria (4). Viable neutrophils secrete NETs within minutes, which appear to trap bacteria and augment killing by retaining the microorganism in close proximity to a variety of anti-microbial granule proteins (4). These delicate NETs are primarily composed of DNA, as well as histones and granule proteins, but do not contain actin. In distinct contrast, the polymers described herein are comprised of both actin and DNA, do not require the action of granule proteins, are a product of the necrotic neutrophil, and increase the number of surviving *P. aeruginosa* (see FIG. 1A) over a period of days. Fragmentation of the NETs by DNase increased bacterial survival, while disruption of the actin-DNA polymers by DNase reduced biofilm formation. Thus construction of NETs represents an elegant mechanism of successful bacterial killing by the live neutrophil, while actin-DNA enhancement of biofilm formation may represent a maladaptive response to years of relentless accumulation and neutrophil death in the CF airway.

Although the neutrophil contains a number of proteins with significant anti-microbial potential, it appears that successful bacterial killing by granule proteins is highly dependent on the extracellular milieu. Recently, purified lactoferrin, a major component of the secondary neutrophil granules, was found to prevent *P. aeruginosa* biofilm development (39). Although lactoferrin is relatively abundant in CF sputum, it is only one of at least 50 proteins contained within neutrophil granules (3), and its inhibitory effect was not evident when the total content of neutrophil granules were combined with *P. aeruginosa* (FIG. 3A). It is likely that during *Pseudomonas*-induced neutrophil necrosis, lactoferrin (and other potential beneficial proteins) are degraded by neutrophil- and *Pseudomonas*-derived proteases (5, 44).

The unique environment of the CF airway exerts selective pressures, which can result in profound genetic alterations within the bacteria. *P. aeruginosa* strains isolated at the time of initial infection resemble environmental strains, which are motile, nonmucoid, lack antibiotic resistance, and have a smooth-type penta-acylated LPS. After years of infection, "CF-strains" of *P. aeruginosa* emerge, with an extensive array of altered phenotypes (6), including a mucoid, nonmotile phenotype, extensive resistance to antibiotics, and a rough-type, arabinomannan-modified, hexa/hepta-acylated LPS (11, 14). The PA01 strain used in the studies described herein clearly resembles the environmental strains of early infection. Without being bound by theory, the present inventors' believe it is of importance that the enhancement of biofilm formation described here is achieved with a non-mucoid, non-CF strain of *P. aeruginosa*, as this may represent a mechanism that allows environmental strains to initially persist in the CF airway. Once present in the biofilm form, environmental *P. aeruginosa* strains would have the opportunity to adapt to the intense inflammatory conditions and antibiotic treatment over decades without eradication.

Therefore, one embodiment of the present invention comprises administering to the patient, either directly or by application to a carrier, implant, catheter, medical device, or tissue or wound dressing: a compound that inhibits the formation or polymerization of actin microfilaments or depolymerizes actin microfilaments, at or proximal to the site of biofilm formation. The method can further comprise, or alternatively include, a compound that inhibits the accumulation of, necrosis of, and/or release of cellular content of cells that undergo necrosis, at or proximal to the site of bacterial infection and/or biofilm formation. The method can further comprise, in combination with one or both of the compounds above, the administration of an anti-DNA compound and/or an anti-mucin compound and/or another compound that is useful for the prevention and/or treatment of a disease or condition in the patient, or that is useful in connection with a procedure being performed on the patient.

Preferably, the cells that undergo necrosis and are targeted by the method of the invention are neutrophils, although other types of cells that can undergo necrosis at a site of microbial infection are also included in the invention. For example, such other cells include, but are not limited to, airway epithelial cells or other epithelial cells, macrophages, monocytes, lymphocytes, eosinophils, and the infectious microbe itself (e.g., *P. aeruginosa*).

A biofilm is generally defined herein as a community of microorganisms attached to a solid surface. A biofilm community can include bacteria, fungi, yeasts, protozoa, and other microorganisms. More specifically, a biofilm is a surface-attached community of microbial cells encased within a self-produced extracellular polysaccharide matrix that exhibits properties different from the planktonic microbial counterparts. Biofilms that are commonly found associated with human tissue and organ surfaces are frequently bacterial biofilms. In cystic fibrosis, by way of example, both *Pseudomonas aeruginosa* and *Burkholderia multivorans* infect and form biofilms in the lungs of patients having the disease. Other examples of microorganisms that form biofilms in tissues or on medical devices or dressings include, but are not limited to: *Streptococcus sanguis, E. coli*, and *Streptococcus viridans*.

The method of the present invention can be used to treat any patient (subject, individual, animal) that has, is developing (biofilm formation is clinically evident or detectable to the skilled artisan, but has not yet fully formed), or is at risk of developing (no biofilm formation is yet detectable to the clinician or skilled artisan, but the subject is known to be at risk of developing a biofilm due to disease or the pending performance of a treatment, such as a graft implantation). The term "patient" typically refers to a subject that is to be treated or is being treated by a clinician (doctor, nurse, or other medical practitioner) for a disease, condition, procedure, or routine examination (i.e., the patient need not be ill or otherwise suffering from any disease or condition to be treated). However, as used herein, the terms "patient", "subject", "individual" and "animal" can be generally be used interchangeably with reference to the subject to which a compound of the invention is to be administered.

Microbial biofilms can form in and on a variety of tissues as well as on or in a variety of devices and materials that may be used during the treatment of a subject for a particular disease or condition. For example, the method of the present invention can be used to prevent or reduced biofilm formation, or to reduce existing or developing biofilms that may form in connection with a disease or condition in an organ, tissue or body system including, but not limited to, lung, urinary tract, head and neck, vascular system, bone, skin, abdomen. Biofilms may also form on the surface of a tissue, organ or bodily part including, but not limited to, lung, medium airways, ureter, urethra, bladder, prostate, mouth, ear, heart valve, vein, joint, bone, skin, and bile duct. Biofilms may form in connection with a disease or condition including, but not limited to: infectious kidney stones, cystitis, catheter-related infection (kidney, vascular, peritoneal), medical device-related infections, prostatitis, dental caries, chronic otitis media, cystic fibrosis, bronchiectasis, bacterial endocarditis, Legionnaire's disease, orthopedic implant infection, osteomyelitis, wounds, acne, and biliary stents. All of these scenarios are encompassed by the present invention.

Preferably, the compound is administered to a subject (patient, individual, animal) prior to the development of a biofilm, or at the earliest time that biofilm development is suspected or detected. Without being bound by theory, the present inventors believe that the method of the present invention will be particularly effective when used as a preventative or early stage inhibition of biofilm formation. For example, the method of the invention can be used when a patient is suspected to have or be developing a disease or condition associate with the formation of biofilms, where the method is used when the diagnosis made or early treatment is performed (e.g., prior to the establishment of biofilms in the patient, although there may be detectable evidence of biofilm formation). A young patient diagnosed with cystic fibrosis, for example, may develop biofilms after several years of the disease, but during the earlier diagnosis and treatment stages, the method of the invention may prevent or reduce the formation of the biofilms as the disease advances in the patient. As another example, the method of the present invention may be applied to a prosthetic graft or used in a patient receiving the graft prior to or during the implantation or utilization of the graft. Similarly, the method of the present invention can be used when prior to or during use of a catheter by a patient, by applying the compound to the catheter and/or on the tissue contacting or near the catheter. The compound could also be applied to the site of a wound or to the wound dressing when the wound is initially and subsequently treated, or the compound can be applied to a medical device that contacts a patient tissue surface prior to or during use of the medical device by a patient.

For the inhibition of the formation or polymerization of actin microfilaments (or depolymerization of the actin microfilaments), compounds preferably inhibit F-actin, which is the microfilament form of actin, and can also be referred to herein as "anti-actin" compounds. A variety of compounds that affect the polymerization and depolymerization of actin filaments are well known in the art. A detailed description of various classes of such compounds, as well as specific compounds and their known actions on actin is provided in Meijer et al., 2003, *Progress in Cell Cycle Research* 5:511-525, which is incorporated herein by reference in its entirety. Classes of compounds that can be used in the present invention include, but are not limited to, cytochalasins, latrunculins, misakinolides, swinholides, myacolides, spinxolides, and scytophycins. Specific compounds which are useful in a product/composition/formulation of the present invention include, but are not limited to, cytochalasin B, cytochalasin D, latrunculin A, misakinolide A, swinholide A, myacolide B, spinxolide, scytophycin, domain 1 of gelsolin, destrin or profilin. Other suitable anti-actin compounds will be known to those of skill in the art or can be identified using standard actin polymerization assays (e.g., see Meijer et al., supra) and such compounds are encompassed for use in the present invention.

For the inhibition of neutrophil accumulation, necrosis and/or release of cellular content, or for the inhibition of many other necrotic cell types targeted by the invention (cells that can undergo necrosis at the site of a microbial infection), any anti-inflammatory compound or any compound that interferes with a neutrophil's (by way of example) ability to adhere to or near a site of infection by biofilm-associated microbe, to migrate to such site, or to sense or respond to chemoattractants at or near such site (or that would result in migration of the neutrophil to such site), is encompassed by the present invention. For example, such compounds can inhibit or reduce the release or biological activity of chemoattractants, cytokines, or chemokines at or near (proximal to) the site of infection that would otherwise attract a neutrophil, cause it to migrate to the site of infection, or allow or enhance neutrophil adherence at or near the site of infection. Administration of such anti-inflammatory/anti-neutrophil compounds early in the disease process that is associated with biofilm formation is believed to be an important aspect of the invention. Therefore, anti-inflammatories/anti-neutrophil compounds would be administered upon the initial diagnosis of the disease or condition that is associated with biofilm formation, and preferably prior to a significant formation of biofilms in the patient.

Such compounds are well known in the art and include, but are not limited to, cytokine inhibitors, chemokine inhibitors, chemoattractant inhibitors, fluoroquinolones, Cox inhibitors, leukotiene receptor antagonists, leukotriene synthesis inhibitors, inhibitors of the p38 MAP kinase pathway, and glucocorticoids. More specifically, compounds that are useful in this embodiment of the invention include, but are not limited to: any inhibitor of eicosanoid synthesis and release, including any Cox-2 inhibitor; Cox-1 inhibitors; inhibitors of some certain prostaglandins (prostaglandin E(2); PGD(2)), inhibitors of certain leukotrienes ($LTB_4$); classes of antibiotics with known direct or indirect anti-inflammatory effects, including macrolides (e.g. azithromycin) and fluoroquinolones (e.g., levofloxacin; moxifloxacin; gatifloxacin); inhibitors of p38 MAP kinase; antagonists of growth factors which regulate neutrophil release, including granulocyte colony-stimulating factor (G-CSF) (e.g., antibodies or antigen binding fragments thereof, G-CSF antagonist variants or mimetics, drugs that antagonize the function of G-CSF); antagonists of granulocyte-macrophage colony-stimulating factor (GM-CSF); inhibitors of the function of cytokines and chemokines, including antagonists of tumor necrosis factor (TNF), antagonists of interleukin-8 (IL-8); transforming growth factor beta (TGF-beta); antibodies that block sites of neutrophil adhesion and thereby limit neutrophil accumulation to sites of inflammation, including anti-beta2 integrins (e.g., anti-CD11/CD18) and anti-ICAM-1; and neutrophil inhibitory material from other organisms, (e.g., excretory-secretory (ES) material from the parasitic nematode *Nippostrongylus brasiliensis*).

In one embodiment, a product, composition or formulation of the present invention also includes an anti-DNA compound. According to the present invention, an anti-DNA compound is any compound that causes the destabilization or degradation of DNA. Such compounds are known in the art and include, but are not limited to, nucleases, hydroxyl radical generating compounds, and the like. For example, DNase I or rhDNase (Pulmozyme; Genentech, USA) is a well-known anti-DNA compound that is useful in the present invention. Compounds suitable for the degradation of DNA will be known to those of skill in the art and all are encompassed by the present invention.

In another embodiment, a product, composition or formulation of the present invention also includes an anti-mucin compound. Mucins are a family of large, heavily glycosylated proteins. Some mucins are membrane bound due to the presence of a hydrophobic membrane-spanning domain that favors retention in the plasma membrane, but many mucins are secreted on mucosal surfaces and in saliva. Anti-mucin compounds include any compound that causes the destabilization or degradation of mucin, or inhibits the interaction of mucin with other compounds or molecules. Such compounds include, but are not limited to, antibodies and antigen binding fragments thereof that bind to mucin, sulphatases, glycosidases, and proteases.

In another embodiment, a product, composition or formulation of the present invention also includes one or more compounds that are useful for treating a particular disease or condition that is associated with biofilm formation. For example, when the patient has or is suspected of having cystic fibrosis, the anti-actin compound and/or anti-inflammatory/anti-neutrophil compound can be used in conjunction with other drugs or therapeutic compounds that are conventionally used to treat cystic fibrosis. As another example, when the patient has a wound, the anti-actin compound and/or anti-inflammatory/anti-neutrophil compound can be applied to the wound dressing, along with other compounds, such as anti-microbial compounds, or administered concurrently with other such compounds by a different route. As yet another example, patients receiving a prosthetic graft may be receiving anti-rejection drugs, anti-microbials, or growth factors to enhance the establishment of the graft or growth of appropriate tissue at the graft site, and the anti-actin compound and/or anti-inflammatory/anti-neutrophil compound of the invention can be administered in connection with such treatments.

According to the present invention, the present invention can use any one, two, three, four, or more compounds from any class listed above, including any combination of the compounds. For example, in a preferred embodiment, the method uses both an anti-actin microfilament compound and an anti-DNA compound and/or an anti-mucin compound. Alternatively, the method uses both an anti-actin microfilament compound and an anti-neutrophil (or other necrotic cell) compound. In another aspect, the method uses an anti-neutrophil (or other necrotic cell) compound and an anti-DNA compound and/or an anti-mucin compound. In further embodiments, additional compounds that are useful for the treatment of a particular condition or disease in the patient to be treated can be included.

According to the present invention, an "antagonist" or an "anti"-compound or agent (e.g., an anti-actin microfilament compound, an-anti-neutrophil compound, an anti-DNA compound or an anti-mucin compound) refers to any compound which inhibits (e.g., antagonizes, reduces, decreases, blocks, reverses, or alters) the effect of a given protein or compound. More particularly, an antagonist is capable of acting in a manner relative to the given protein's or compound's activity, such that the biological activity of the given protein or compound, is decreased or blocked in a manner that is antagonistic (e.g., against, a reversal of, contrary to) to the natural action of the given protein or compound. Antagonists can include, but are not limited to, an antibody or antigen binding fragment thereof, a protein, peptide, nucleic acid (including ribozymes and antisense), or a product of drug/compound/peptide design or selection that provides the antagonistic effect.

Antagonists useful in the present invention also include compounds that are products of rational drug design, natural products, and compounds having partially defined regulatory properties. A regulatory agent, including an antagonist of a given protein, can be a protein-based compound, a carbohydrate-based compound, a lipid-based compound, a nucleic acid-based compound, a natural organic compound, a synthetically derived organic compound, or an antibody, or fragments thereof. In one embodiment, such regulatory agents of the present invention include drugs, including peptides, oligonucleotides, carbohydrates and/or synthetic organic molecules which regulate the production and/or function of one or more proteins in the alternative complement pathway. Such an agent can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the same building blocks) or by rational drug design. See for example, Maulik et al., 1997, *Molecular Biotechnology: Therapeutic Applications and Strategies*, Wiley-Liss, Inc., which is incorporated herein by reference in its entirety.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands against a desired target, and then optimize the lead molecules by either random or directed design strategies. Methods of molecular diversity are described in detail in Maulik, et al., supra.

In a rational drug design procedure, the three-dimensional structure of a regulatory compound can be analyzed by, for example, nuclear magnetic resonance (NMR) or X-ray crystallography. This three-dimensional structure can then be used to predict structures of potential compounds, such as potential regulatory agents by, for example, computer modeling. The predicted compound structure can be used to optimize lead compounds derived, for example, by molecular diversity methods. In addition, the predicted compound structure can be produced by, for example, chemical synthesis, recombinant DNA technology, or by isolating a mimetope from a natural source (e.g., plants, animals, bacteria and fungi).

Various other methods of structure-based drug design are disclosed in Maulik et al., 1997, supra. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

An antibody or antigen binding fragment thereof useful in the present invention selectively binds to a protein and thereby blocks or inhibits the activity of the protein. According to the present invention, the phrase "selectively binds to" refers to the ability of an antibody, antigen binding fragment or binding partner to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or $F(ab)_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention. A bi-specific (or multi-specific) antibody is capable of binding two (or more) antigens, as with a divalent (or multivalent) antibody, but in this case, the antigens are different antigens (i.e., the antibody exhibits dual or greater specificity). A bi-specific antibody suitable for use in the present method includes an antibody having: (a) a first portion (e.g., a first antigen binding portion) which binds to a given protein; and (b) a second portion which binds to a second protein.

The invention also extends to non-antibody polypeptides, sometimes referred to as antigen binding partners or antigen binding polypeptides, that have been designed to bind selectively to and cause the neutralization or inhibition of a protein according to the present invention. Examples of the design of such polypeptides, which possess a prescribed ligand specificity are given in Beste et al. (*Proc. Natl. Acad. Sci.* 96:1898-1903, 1999), incorporated herein by reference in its entirety.

An isolated nucleic acid molecule that is useful as an antagonist includes, but is not limited to, an anti-sense nucleic acid molecule, a ribozyme or siRNA. As used herein, an anti-sense nucleic acid molecule is defined as an isolated nucleic acid molecule that reduces expression of a protein by hybridizing under high stringency conditions to a gene encoding the protein. Such a nucleic acid molecule is sufficiently similar to the gene encoding the protein that the molecule is capable of hybridizing under high stringency conditions to the coding or complementary strand of the gene or RNA encoding the natural protein. RNA interference (RNAi) is a process whereby double stranded RNA, and in mammalian systems, short interfering RNA (siRNA), is used to inhibit or silence expression of complementary genes. In the target cell, siRNA are unwound and associate with an RNA induced silencing complex (RISC), which is then guided to the mRNA sequences that are complementary to the siRNA, whereby the RISC cleaves the mRNA. A ribozyme is an RNA segment that functions by binding to the target RNA moiety and inactivate it by cleaving the phosphodiester backbone at a specific cutting site.

An isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated nucleic acid molecule can be isolated from its natural source or produced using recombinant DNA technology (e.g., polymerase chain reaction (PCR) amplification, cloning) or chemical synthesis.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid., is incorporated by reference herein in its entirety.

In one embodiment of the invention, a method is provided to identify compounds that are useful in the method of inhibiting the formation of biofilms that are enhanced by necrotic cells, such as neutrophils, or reducing existing or developing such biofilms. This method includes the steps of: (a) contacting a putative inhibitory compound with a microbial culture in the presence and absence of a population of cells or a lysate thereof; and (b) measuring biofilm formation after contact with the putative regulatory compound as compared to in the absence of the compound and as compared to in the presence and absence of the population of cells or lysate thereof. A decrease in biofilm formation in the presence of the putative regulatory compound and the presence of the population of cells or lysate thereof, as compared to in the absence of the population of cells or lysate thereof and as compared to in the absence of the putative regulatory compound, indicates that the putative regulatory compound inhibits necrotic cell-enhanced biofilm formation or reduces necrotic cell-enhanced biofilms. In this embodiment of the invention, the microbial culture must be a microbial culture that can form biofilms, but the culture is provided in a planktonic state prior to contact with the putative inhibitory compound. In addition, the population of cells used in this assay are selected because they can undergo necrosis in the presence of the microbial cells. For example, as shown in the examples, neutrophils will undergo necrosis in the presence of a culture of *P. aeruginosa*. These are only exemplary microbe and cell combinations that can be used. Other combinations will be apparent to those of skill in the art. The assay of the invention is designed to identify compounds that inhibit biofilm formation that is associated with or enhanced by the necrosis of cells at the site of infection or biofilm formation.

Preferred microbial cells for use in this invention are any microbial cells that are capable of forming biofilms under some conditions, and particularly, including in the presence of necrotic cells or the components thereof (e.g., actin microfilaments or DNA) as described herein. Preferably, formation of biofilms and aggregation of the microbial cells is enhanced by the necrotic cells or components thereof. The microbial cells are not required to be of the same strain, species, genus, or even microbe, although this is preferred. Microbial cells that form biofilms can include, but are not limited to, bacteria, fungi, yeasts, and protozoa, with bacteria being particularly preferred. Bacteria that are particularly useful in this method of the invention include, but are not limited to, any of the previously described biofilm forming bacteria, such as *P. aeruginosa, Burkholderia multivorans, Streptococcus sanguis, E. coli,* and *Streptococcus viridans*. In one embodiment, particular strains or mutants of a microbial cell can be used in the assay to identify compounds that impact necrotic cell-enhanced biofilm formation that may be relevant to a particular strain of microbial cell carried by a specific patient or subset of patients, or to focus the identification of the inhibitor on a particular characteristic or expression of a particular gene or protein in the microbial cell that affects necrotic cell-enhanced biofilm formation. In one embodiment, the cells can be labeled with a detectable label (e.g., green fluorescent protein).

Preferred populations of cells (or the lysates thereof) to be used in the present invention include any cells that can undergo necrosis in the presence of a microbial cell as described above. For example, such cells include, but are not limited to, neutrophils, airway epithelial cells or other epithelial cells, macrophages, monocytes, lymphocytes, eosinophils, and the infectious microbe itself (e.g., *P. aeruginosa*). Cell lysates can be produced using any methods known to those of skill in the art, including any means of disrupting, permeabilizing or otherwise lysing of cell membranes to release the intracellular contents. In one embodiment, the cells can be labeled with a detectable label.

As used herein, the term "test compound", "putative inhibitory compound" or "putative regulatory compound" refers to compounds having an unknown or previously unappreciated regulatory activity in a particular process. As such, the term "identify" with regard to methods to identify compounds is intended to include all compounds, the usefulness of which as a regulatory compound for the purposes of regulating biofilm formation is determined by a method of the present invention.

The conditions under which a microbial cell are contacted with a putative regulatory compound according to the present invention, such as by mixing, plating, etc., are conditions in which the microbial cell is not forming a biofilm (i.e., the microbial culture is in a planktonic state) if essentially no regulatory compound is present. The conditions under which the population of cells that can undergo necrosis are contacted with a putative regulatory compound are conditions under which the majority of cells in the population of cells are viable and not undergoing necrosis.

The present methods involve contacting cells and/or lysates with the compound being tested for a sufficient time to allow for interaction of the compound with the microbial cells and/or the population of cells or components in the lysate thereof. The period of contact with the compound being tested can be varied depending on the result being measured, and can be determined by one of skill in the art. As used herein, the term "contact period" refers to the time period during which cells are in contact with the compound being tested. The term "incubation period" refers to the entire time during which cells are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring.

The final step in the method is to measure biofilm formation or a parameter associated with biofilm formation in the presence and absence of the putative regulatory compound and in the presence and absence of the population of cells. Since the present method is designed to identify compounds that impact necrotic cell-enhanced biofilm formation (although the compound may also affect biofilm formation in the absence of necrotic cells), a candidate compound is identified as useful if it inhibits biofilm formation to a greater degree (detectable, and preferably, statistically significantly greater) in the presence of the necrotic cells as compared to in the absence of the necrotic cells. Statistical analysis to determine differences between controls and test cultures can be performed using any methods known in the art, including, but not limited to, Student's t test or analysis of variance for continuous variables. Statistical significance is typically defined as $p<0.05$.

In another, or additional embodiment, one can detect the effect of the putative regulatory compound on the binding of the microbial cells to actin and/or DNA from the population of necrotic cells, or on the aggregation of microbial cells in the presence of the population of necrotic cells.

Methods of evaluating biofilm formation are well known in the art and are described in the Examples. For example, confocal microscopy, microscopy, and static biofilm assays. Methods of measuring actin and DNA binding are also well known in the art and are described in the Examples.

Agonists and antagonists identified by the above methods or any other suitable method are useful in the therapeutic or biofilm-inhibition methods as described herein.

Compounds useful in the present invention are typically provided in the form of a composition (formulation). In one embodiment of the invention, a pharmaceutical composition or formulation is prepared from an effective amount of a compound of the invention and a pharmaceutically-acceptable carrier. Pharmaceutically-acceptable carriers are well known to those with skill in the art. According to the present invention, a "pharmaceutically acceptable carrier" includes pharmaceutically acceptable excipients and/or pharmaceutically acceptable delivery vehicles, which are suitable for use in the administration of a formulation or composition to a suitable in vivo site. A suitable in vivo site is preferably any site wherein biofilms have formed, are forming, or may form. Preferred pharmaceutically acceptable carriers are capable of maintaining a compound used in a formulation of the invention in a form that, upon arrival of the compound at the target site in a patient, the compound is capable of acting, preferably resulting in a therapeutic benefit to the patient.

One type of pharmaceutically acceptable carrier includes a controlled release formulation that is capable of slowly releasing a composition of the present invention into a patient. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other suitable carriers include any carrier that can be bound to or incorporated with the compound that extends that half-life of the compound to be delivered. A carrier can be modified to target to a particular site in a patient, thereby targeting and making use of a compound at that site.

In one embodiment, a compound useful in the present method is administered in a formulation suitable for aerosol delivery. Carriers that are particularly useful for aerosol delivery according to the present invention include, but are not limited to: dry, dispersible powders; small capsules (e.g., microcapsules or microparticles); liposomes; and nebulized sprays. Dry, dispersible powders suitable for aerosolized delivery of compounds are described in detail in U.S. Pat. No. 6,165,463, incorporated herein by reference in its entirety (See also products from Inhale Therapeutic Systems, Inc. and Quadrant Technology). Suitable liposomes for use in aerosols include any liposome, and particularly, any liposome that is sufficiently small to be delivered by aerosol in the method of the invention. Microcapsules and microparticles are known in the art. For example, Alliance Pharmaceutical Corporation has a particle engineering technology, called PulmoSphere, prepared by a proprietary spray-drying process and are designed to be both hollow and porous. A product by Ventolin consists of micronized albuterol (free base) particles suspended in a mixture of CFC-based propellants. Proventil HFA contains micronized albuterol sulfate and a small percentage of an ethanol co-solvent to solubilize the stabilizing oleic acid surfactant. Devices for delivery of aerosolized formulations include, but are not limited to, pressurized metered dose inhalers (MDI), dry powder inhalers (DPI), and metered solution devices (MSI), and include devices that are nebulizers and inhalers.

In another embodiment, a compound useful in the present method is administered in a formulation suitable for topical delivery. Such formulations include any lotion, excipient, cream, gel, or other topical carrier suitable for topical administration.

For injection, the compounds of the invention can be formulated in appropriate aqueous solutions, such as physiologically compatible buffers such as Hanks's solution, Ringer's solution, or physiological saline buffer.

For transmucosal and transcutaneous administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

The compounds can be formulated for parenteral administration by injection, e.g., by bolus injection or continuous infusion. Formulations for injection can be presented in unit dosage form, e.g., in ampoules or in multi-dose containers, with an added preservative.

The compounds can also be formulated in rectal compositions such as suppositories or retention enemas, e.g., containing conventional suppository bases such as cocoa butter or other glycerides.

In accordance with the present invention, determination of acceptable protocols to administer a compound (product, agent, composition, formulation), including the route of administration and the effective amount of a compound to be administered to a patient, can be accomplished by those skilled in the art. A compound of the present invention can be administered in vivo or ex vivo. Suitable in vivo routes of administration can include, but are not limited to, oral, nasal, inhaled, topical, intratracheal, transdermal, rectal, and parenteral routes. Preferred parenteral routes can include, but are not limited to, subcutaneous, intradermal, intravenous, intramuscular, and intraperitoneal routes. Preferred topical routes include inhalation by aerosol (i.e., spraying) or topical surface administration to the skin of a patient, or to a dressing, device, catheter, prosthetic graft or other product to be placed into contact with a patient tissue surface. Preferably, a compound is administered by nasal, inhaled, intratracheal, topical, or systemic routes (e.g., intraperitoneal, intravenous). Ex vivo refers to performing part of the administration step outside of the patient.

Preferably, the compound is administered directly to or proximal to the site of biofilm formation or potential therefore. For example, the biofilm can be administered by surgical or clinical procedure directly to the tissue, organ, bodily part, or to a material or device that is to be (or anticipated to be) at or proximal to a site in the patient where a biofilm may form, is likely to form, or will form. By way of example, in one aspect, the compound is administered to the lung or airways of the patient. In another aspect, the compound is applied to a prosthetic graft or administered to the patient receiving the graft prior to or during the implantation or utilization of the graft. In another aspect, the compound is applied to a catheter prior to or during use of the catheter by a patient. In yet another aspect, the compound is applied to the site of a wound or to the wound dressing when the wound is treated. A compound may also be applied to a medical device that contacts a patient tissue surface prior to or during use of the medical device by a patient. Other types of administration or application of the compound and method of the invention will be apparent to those of skill in the art given this discussion.

An effective amount is any amount of the compound that causes a detectable reduction in biofilm formation as compared to in the absence of the compound, or reduces existing biofilms or developing biofilms as compared to in the absence of the compound. A preferred single dose of an agent, including proteins, small molecules and antibodies, for use in a method described herein, comprises between about 0.01 microgram×kilogram$^{-1}$ and about 10 milligram×kilogram$^{-1}$ body weight of an animal. A more preferred single dose of an agent comprises between about 1 microgram×kilogram$^{-1}$ and about 10 milligram×kilogram$^{-1}$ body weight of an animal. An even more preferred single dose of an agent comprises between about 5 microgram×kilogram$^{-1}$ and about 7 milligram×kilogram$^{-1}$ body weight of an animal. An even more preferred single dose of an agent comprises between about 10 microgram×kilogram$^{-1}$ and about 5 milligram×kilogram$^{-1}$ body weight of an animal. A particularly preferred single dose of an agent comprises between about 0.1 milligram×kilogram$^{-1}$ and about 5 milligram×kilogram$^{-1}$ body weight of an animal, if the an agent is delivered by aerosol. Another particularly preferred single dose of an agent comprises between about 0.1 microgram×kilogram$^{-1}$ and about 10 microgram×kilogram$^{-1}$ body weight of an animal, if the agent is delivered parenterally.

In one embodiment, an appropriate single dose of a nucleic acid, when delivered with a liposome carrier, is from about 0.1 μg to about 100 μg per kg body weight of the patient to which the complex is being administered. In another embodiment, an appropriate single dose is from about 1 μg to about 10 μg per kg body weight. In another embodiment, an appropriate single dose of nucleic acid:lipid complex is at least about 0.1 μg of nucleic acid, more preferably at least about 1 μg of nucleic acid, even more preferably at least about 10 μg of nucleic acid, even more preferably at least about 50 μg of nucleic acid, and even more preferably at least about 100 μg of nucleic acid.

One of skill in the art will be able to determine that the number of doses of a compound to be administered to an animal is dependent upon the extent of the biofilm formation and the underlying condition or disease of which biofilm formation is a symptom or a component, and the response of an individual patient to the treatment. In addition, the clinician will be able to determine the appropriate timing for delivery of the compound in a manner effective to inhibit biofilm formation or reduce biofilms in the patient. Preferably, the compound is delivered within between about 1 hour and 48 hours of the diagnosis or confirmation by a clinician of the risk or likelihood of developing biofilms or a condition or disease that is associated with the development of biofilms, or the as soon as an infection has been identified that would be likely to be associated with biofilms, or as soon thereafter as practical in order to inhibit biofilm formation before it develops or before it begins to have a deleterious effect on the patient. When a medical device (graft, catheter, stent, wound dressing, prosthetic) is to be introduced into contact with a patient tissue surface, the compound is preferably administered prior to, concurrently with, or substantially immediately after the patient is contacted with the device, graft or dressing. In one embodiment, the compound is administered as soon as it is recognized (i.e., immediately or in a few hours or days) by the patient or clinician that the patient may be at risk of or developing biofilms. Preferably, such administrations are given until the patient is no longer at risk of developing biofilms or at least until signs of biofilm inhibition or prevention occur. Preferably, the compound is administered within at least 15 minutes, 30 minutes, 45 minutes, 1 hour, 2 hours, 3 hours, or any increment of 0.25 hours from 0.25 hours (15 minutes) to 72 hours prior to or after the diagnosis, procedure or treatment of the patient. The compound can be administered subsequently, routinely, or as needed to prevent, control or reduce biofilm formation or reduce existing or developing biofilms in the patient.

Typically, it is desirable to obtain a therapeutic benefit in a patient. A therapeutic benefit is not necessarily a cure for a particular disease or condition, but rather, preferably encompasses a result which can include alleviation of the disease or condition, elimination of the disease or condition, reduction of a symptom associated with the disease or condition (e.g., biofilm formation), prevention or alleviation of a secondary disease or condition resulting from the occurrence of a primary disease or condition, and/or prevention of the disease or condition. A beneficial effect can easily be assessed by one of ordinary skill in the art and/or by a trained clinician who is treating the patient. The term, "disease" refers to any deviation from the normal health of the individual and includes a state when disease symptoms are present, as well as conditions in which a deviation (e.g., infection, gene mutation, genetic defect, etc.) has occurred, but symptoms are not yet manifested. As used herein, the phrase "protected from a disease" refers to reducing the symptoms of the disease; reducing the occurrence of the disease, and/or reducing the severity of the disease. Protecting a patient can refer to the ability of a compound or composition of the present invention, when administered to a patient, to prevent a condition from occurring and/or to cure or to alleviate the symptoms of the disease or condition, signs or causes. As such, to protect a patient from a disease includes both preventing disease occurrence (prophylactic treatment) and treating a patient that has a disease (therapeutic treatment) to reduce the symptoms of the disease. More specifically, protecting a patient from biofilm formation can refer to preventing the formation or development of a biofilm and/or to reduce or eliminate existing biofilms in the patient. To treat a patient refers to the act of applying the method of the invention to any suitable patient (subject, individual, animal).

In one embodiment of the method of the invention, in a patient that has or is developing a biofilm, the particular microbial strain can be identified prior to administration of the compound. As described in the Examples section, various strains of the same microbe may have a variation in the biofilm response to the presence of necrotic cells (e.g., neutrophils), as compared to other strains. The compound used to inhibit the accumulation of, necrosis of, or release of the cellular contents of, cells that undergo necrosis can be selected or modified based on this response, or the dosage or administration protocol may be determined or refined based on this response. For example, one may use the patient isolate to identify compounds from a selection of compounds that are identified as being particularly useful to inhibit necrotic cell-enhanced biofilm formation in the specific patient.

The methods of the present invention can be used in any animal (patient, subject, individual), and particularly, in any animal of the Vertebrate class, Mammalia (i.e., mammals), including, without limitation, primates, rodents, livestock and domestic pets. Preferred mammals to which the present method can be applied are humans.

Various aspects of the present invention are described in the following experiments. These experimental results are for illustrative purposes only and are not intended to limit the scope of the present invention.

EXAMPLES

The following Materials and Methods were used in Examples 1-4 below.

P. aeruginosa and Neutrophil

P. aeruginosa used was strain PA01 (a motile piliated strain) or an isogenic strain of PA01 carrying the gene encoding GFP (31). Human neutrophils were isolated from healthy volunteers, purified by the plasma Percoll method (21) and resuspended in RPMI 1640 (Bio-Whittaker, Walkersville, Md.) supplemented with 10 mM HEPES (pH 7.6) and 2% heat-inactivated platelet-poor plasma.

Biofilm Assays

A static biofilm assay was used with polypropylene tubes (9). PA01 was grown overnight under constant rotation to late stationary phase at 37° C. in LB. All biofilm studies were initiated with neutrophils ($1\times10^7$ cells/ml) and PA01 ($1\times10^6$ CFU/ml) in suspension, and cultures were incubated under stationary conditions at 37° C. P. aeruginosa adherent to the tube was considered to be a biofilm, while bacteria not adherent to the surface of the tube was considered to be "planktonic". Viable P. aeruginosa biofilm and planktonic cells were quantified by sonicating the adherent bacteria in LB, followed by serial dilution and plating to determine CFUs on Pseudomonas Isolation Agar (Difco, Sparks, Md.). P. aeruginosa biofilm density was quantified by crystal violet (CV) staining (9). The contribution of background staining of neutrophil components, tubes and reagents were subtracted from depicted values. Neutrophils were lysed with 0.1% Tween 20 (BioRad, Hercules, Calif.) for 30 min. Neutrophil lysates relatively depleted of F-actin were prepared by precipitating the F-actin using the F-actin/G-actin In Vivo Biochem Kit (Cytoskeleton, Denver, Colo.). The total protein present in the whole cell lysate and the F-actin depleted lysate was determined by the Bradford Protein Assay (BioRad, Hercules, Calif.). Biofilm exopolysaccharide was determined by total carbohydrate assays as previously described (15).

P. aeruginosa Actin-Binding Assay

Purified G-actin extracted from rabbit skeletal muscle was purchased (Sigma, St. Louis, Mo.) as a lyophilized powder containing 2 mM Tris, pH 8.0, 0.5 mM beta mercaptoethanol, 0.2 mM $CaCl_2$, 0.2 mM ATP, and was redissolved in deionized water at a concentration of 3-4 mg/ml, which maintains the G-form of actin. G-actin was polymerized to F-actin by incubating at room temperature for 1 h in the presence of 50 mM KCl and 2 mM $MgCl_2$ in sterile PBS. G-actin was also incubated at room temperature for 1 hr in the absence of KCl and $MgCl_2$ to prevent polymerization. After 1 hour, F-actin and G-actin were plated on a 96-well microtitre plate and incubated overnight at room temperature. All wells were blocked with 1% BSA for 1 hr before adding the bacteria. P. aeruginosa was labeled with the intracellular fluorescent conjugate carboxy-fluorescein diacetate, succinimidyl ester (CFDA SE) for 45 min (Vybrant CFDA SE Cell Tracer Kit, Molecular Probes, Eugene, Oreg.) and then washed with PBS. Labeled P. aeruginosa ($1\times10^6$) were added to wells coated with either F- or G-actin or PBS (with or without KCl and $MgCl_2$) controls. The plates were incubated for 4 hr at 37° C. and then washed carefully with PBS. The fluorescent intensity of bound P. aeruginosa was measured at 492/517 nm with a plate reader (Bio-Tek Instruments) and the quantity of P. aeruginosa present was determined by a standard curve and expressed as a percent of the total number of P. aeruginosa added to the well. Enhanced F-actin formation on the plates was confirmed by staining with yellow-green-fluorescent NBD phallacidin (Molecular Probes) with relative quantification read at 465/536 nm. Equivalent quantities of total F- and G-actin on the plates were confirmed by exposure of the wells with a mouse anti-pan actin IgG antibody (NeoMakers, Fremont, Calif.) followed by secondary binding with an anti-mouse IgG globulin conjugated with horseradish peroxidase which then binds to the antibody-antigen complex. The excess conjugate was removed by washing, followed by the addition of chromogen/substrate tetramethylbenzidine (TMB) with $H_2O_2$ and read at 450/570 nm. The total quantity of protein was confirmed to be equivalent for all conditions, as measured by the Bradford Assay (BioRad, Hercules, Calif.).

Purification of Granular Proteins and DNA

Genomic DNA was isolated from neutrophils and P. aeruginosa using the DNeasy Tissue Kit (Qiagen, Valencia, Calif.) according to the manufacturer's protocol. Actin and DNA polymerization was performed as described previously (38). Effects of filament cleavage was tested by initially treating the samples with 90 Kunitz units/ml of DNase I (43) and/or 200 nM gelsolin (Sigma) (42). Granule proteins were isolated from homogenized human neutrophils by differential centrifugation in a discontinuous Percoll/sucrose gradient (34). Heavy and light granules were immediately suspended in RPMI media and added to P. aeruginosa.

Microscopy

Samples of sputa from CF patients chronically infected with P. aeruginosa were frozen in liquid nitrogen and stored at −20° C. At the time of analysis, sputa were thawed and resuspended carefully in PBS (1:4 vol/vol ratio) containing $10^7$ CFU/ml of P. aeruginosa labeled with the intracellular fluorescent conjugate (CFDA SE) as described in the actin-binding protocol. Samples were incubated for 4 hours at 37° C., then dried on Superfrost/Plus microscope slides (Fisher Scientific) and stained for 15 min with 10 µl of 0.6 µM Alexa Fluor 546 Phalloidin (Molecular Probes), 10 µl of 0.2 µM DAPI, dilactate (Molecular Probes), to visualize F-actin and DNA. Visualization of actin (546/576 nm), DNA (358/461 nm), and P. aeruginosa (492/517 nm) were performed sequentially on the same field, followed by an "overlay" view at all 3 wavelengths. Neutrophil lysates were also combined with P. aeruginosa labeled with CFDA SE for 4 hrs at 37° C., and staining of F-actin and DNA was conducted as described for CF sputa.

Analysis of P. aeruginosa Biofilms by Confocal Microscopy (CM)

GFP-PAO1 was cultured in 8-chamber polystyrene tissue culture treated glass slides (Falcon, Becton Dickinson Labware, Franklin Lakes, N.J.) alone or with neutrophils. At 48 hrs biofilms were evaluated using a Zeiss Axiovert 200M confocal microscope equipped with Slidebook imaging software (Intelligent Imaging, Denver, Colo.). GFP-PAO1 was excited in the FITC channel at 488/500-550 nm. 3-D reconstruction of biofilms was formed from images captured at 1 μm intervals, with segmentation and reconstruction using version 3.5 SURFdriver software (Kailua, Hi.).

Statistical Analysis

Data were analyzed using JMP software (SAS Institute, Cary, N.C.). Student's unpaired t test (two-tailed) was use to determine significance of neutrophil and neutrophil lysate enhancement of *P. aeruginosa* survival and biofilm development (FIGS. 1A-C, 3A) and binding of *P. aeruginosa* to F-actin (FIG. 4) at individual time points. One-way ANOVA using Dunnett's Method was used to analyze variance of multiple group means to the control group (*P. aeruginosa* alone) for biofilm development (FIGS. 1D-E, 2A-D, 3B-C). For all tests, $p<0.05$ was considered significant.

Example 1

The following example demonstrates the effect of human neutrophils on initial *P. aeruginosa* biofilm development.

Figure 1A:
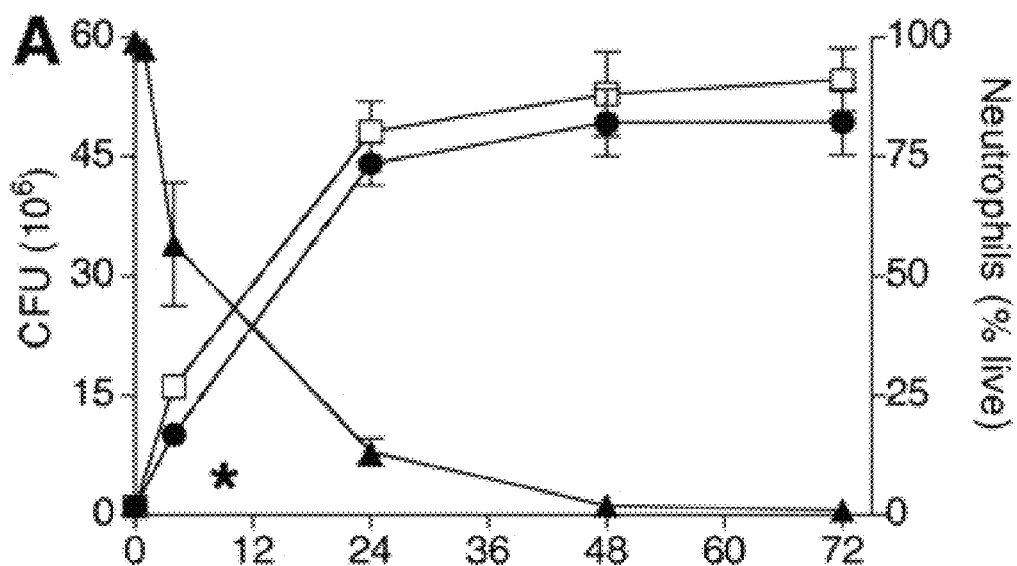
FIG. 1A shows that the presence of neutrophils had little effect on the long-term survival of *P. aeruginosa* (biofilm development of *P. aeruginosa* alone (□); biofilm development of *P. aeruginosa* in the presence of neutrophils (●); neutrophil cytotoxicity (▲)).

Referring to FIG. 1A, biofilm development of *P. aeruginosa* (□) was compared with *P. aeruginosa* in the presence of neutrophils (●). Neutrophil cytotoxicity (▲) equaled 92% after 24 hrs of exposure to *P. aeruginosa* (FIG. 1A; lot (right axis) depicts mean percent of viable neutrophils±SD (n=4)). In the presence of neutrophils, a reduction in the number of surviving *P. aeruginosa* was detected at 4 hours, while at later timepoints, the bactericidal effects of the neutrophil no longer reached significance (FIG. 1A; plot depicts mean±SD of CFU (n=4). *$p<0.05$ by Student's t-test).

Figure 1B:
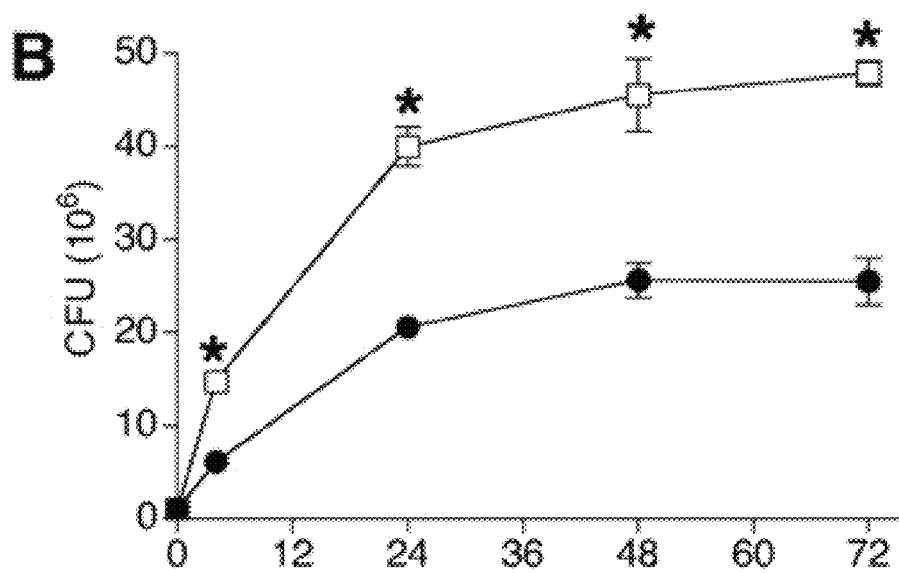
FIG. 1B shows that the presence of neutrophils resulted in fewer viable *P. aeruginosa* in the planktonic state compared to *P. aeruginosa* in the absence of neutrophils (mean±SD of CFU (n=4); *p<0.05) (presence of neutrophils (●); absence of neutrophils (□)).
Figure 1C:
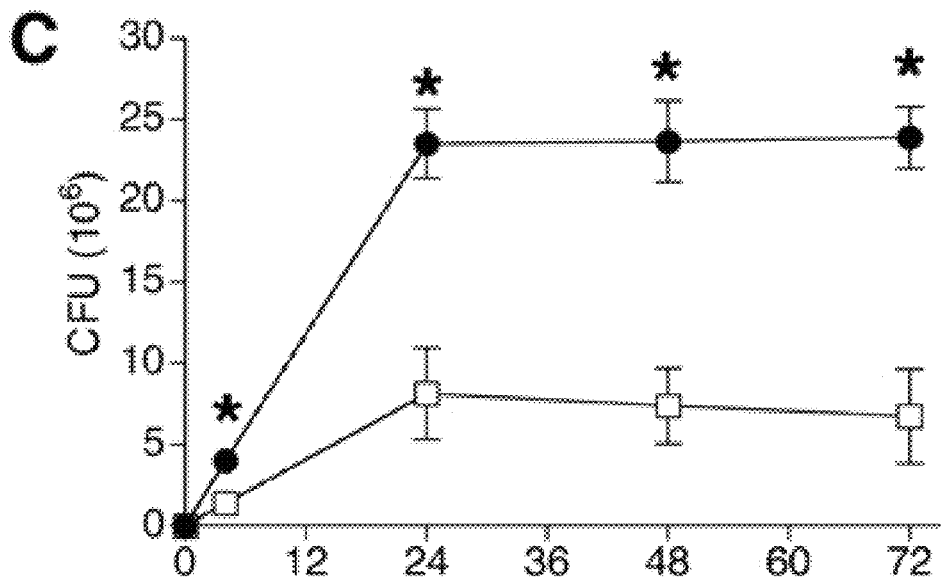
FIG. 1C shows that neutrophils increased the number of viable *P. aeruginosa* in the biofilm state compared to *P. aeruginosa* alone when measured simultaneously with *P. aeruginosa* in the planktonic state shown in FIG. 1B (mean±SD of CFU (n=4); *p<0.05) (biofilm development of *P. aeruginosa* alone (□); biofilm development of *P. aeruginosa* in the presence of neutrophils (●)).

When measured simultaneously, the number of viable *P. aeruginosa* in the planktonic state was significantly decreased by the presence of neutrophils, while the number of viable *P. aeruginosa* in the biofilm state was significantly increased (FIGS. 1B-C). Referring to FIG. 1B, the presence of neutrophils (●) resulted in fewer viable *P. aeruginosa* in the planktonic state compared to *P. aeruginosa* in the absence of neutrophils (□) (plot depicts mean±SD of CFU (n=4). *$p<0.05$ by Student's t-test). Referring to FIG. 1C, neutrophils (●) increased the number of viable *P. aeruginosa* in the biofilm state compared to *P. aeruginosa* alone (□) when measured simultaneously with *P. aeruginosa* in the planktonic state shown in FIG. 1B (plot depicts mean±SD of CFU (n=4). *$p<0.05$ by Student's t-test).

Figure 1D:
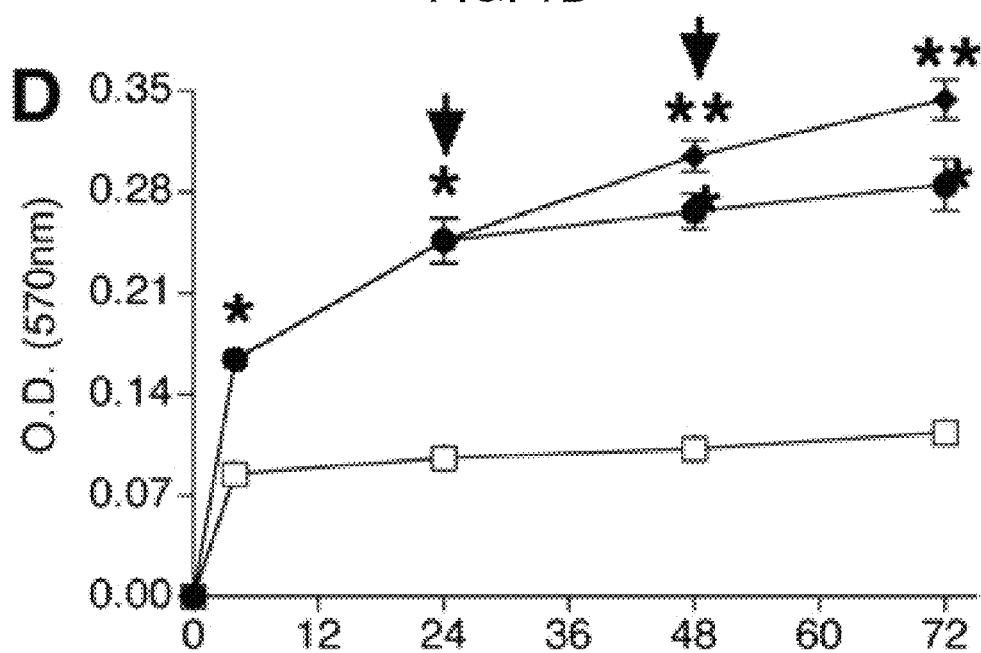
FIG. 1D shows that neutrophils increased biofilm density (assayed by CV staining) compared to *P. aeruginosa* alone by 4 hrs (mean±SD of O.D. measurements (n=21). *p<0.05) (biofilm development of *P. aeruginosa* alone (□); biofilm development of *P. aeruginosa* in the presence of neutrophils (●); additional neutrophils added 24 and 48 hrs (arrows) after the initiation of the biofilm (♦)).

CV staining of *P. aeruginosa* biofilms formed in the presence of neutrophils demonstrated an increase in biofilm density (FIG. 1D; plot depicts mean±SD of O.D. measurements (n=21). *$p<0.05$ by Dunnett's t-test). Specifically, neutrophils (●) increased biofilm density (assayed by CV staining) compared to *P. aeruginosa* alone (□) by 4 hours.

Enhanced biofilm formation in the presence of neutrophils was also demonstrated by quantifying bacterial exopolysaccharide production (FIG. 1E; plot depicts mean±SD of O.D. measurements (n=21). *$p<0.05$ by Dunnett's t-test). Specifically, exopolysaccharide staining of biofilm density demonstrated that the presence of neutrophils (●) resulted in a greater quantity of biofilm compared to *P. aeruginosa* in the absence of neutrophils (□) by 4 hrs.

As neutrophils are recruited continuously to the CF airway, the effect of adding additional viable neutrophils 24 and 48 hrs after initiation of biofilm formation was tested. Supplementing neutrophils to *P. aeruginosa* in the early stages of biofilm development resulted in additional biofilm enhancement (FIGS. 1D-E). When additional neutrophils were added 24 and 48 hrs (arrows) after the initiation of the biofilm, further enhancement of the biofilm density (♦) was observed at 48 and 72 hrs.

For each assay described above, significant enhancement of biofilm development was observed by 4 hours, and by 72 hours the extent of neutrophil-induced biofilm enhancement exceeded 3.5-fold as assessed by viable bacterial colony counts, 2.5-fold as assessed by biofilm density, and 2-fold as assessed by exopolysaccharide content.

Confocal microscopy and 3-D reconstruction of GFP-labeled *P. aeruginosa* biofilms in the presence of neutrophils depicted a thicker and more developed biofilm, when compared to the absence of neutrophils (data not shown). Together, data presented in FIGS. 1 and 2 demonstrate the potential of the neutrophil to enhance the earliest stages of *P. aeruginosa* biofilm formation.

Example 2

The following example shows the enhancement of *P. aeruginosa* biofilm formation by lysed neutrophils.

Since neutrophil necrosis is rapid in the presence of *P. aeruginosa*, the capacity of the cellular content of lysed neutrophils to evoke enhanced *P. aeruginosa* biofilm development was tested. Parameters of biofilm development of *P. aeruginosa* (□) were compared with *P. aeruginosa* in the presence of lysed neutrophils (●) at time intervals from 0 to 72 hrs. Combining *P. aeruginosa* with neutrophil lysates significantly enhanced biofilm formation as measured by CV staining and exopolysaccharide synthesis, and supplementing the early biofilm with additional quantities of lysed neutrophils at 24 and 48 hrs further enhanced biofilm production (FIGS. 2A,C). Referring to FIG. 2A, crystal violet staining of biofilm density demonstrated that the presence of lysed neutrophils resulted in a greater quantity of biofilm compared to *P. aeruginosa* in the absence of neutrophils by 4 hrs. When additional neutrophil lysates (♦) were added 24 and 48 hrs (arrows) after the initiation of the biofilm, further enhancement of the biofilm density was observed at 48 and 72 hrs. Referring to FIG. 2C, exopolysaccharide staining of biofilm density demonstrated that the presence of lysed neutrophils resulted in a greater quantity of biofilm compared to *P. aeruginosa* in the absence of neutrophils by 4 hrs. When additional neutrophil lysates (♦) were added 24 and 48 hrs (arrows) after the initiation of the biofilm, further enhancement of the biofilm density was observed at 48 and 72 hrs.

Biofilms formed in the presence of lysed neutrophils achieved 92% of the biofilm enhancement of an equivalent number of viable neutrophils when assayed by CV staining, and 94% percent when assayed by exopolysaccharide synthesis (FIGS. 2B,D). Furthermore, the number of viable surface attached biofilm cells increased when lysed neutrophils were added, while the number of viable planktonic cells decreased (data not shown). Referring to FIG. 2B, crystal violet staining of biofilm density demonstrated that by 72 hrs, lysed neutrophils added at 0, 24, and 48 hrs (hatched bar) achieved 92% of the biofilm development seen with viable neutrophils added at 0, 24, and 48 hrs (solid bar). Both conditions resulted in significantly greater biofilm development when compared to *P. aeruginosa* in the absence of neutrophils (open bar). Referring to FIG. 2D, exopolysaccharide staining of biofilm density demonstrated that by 72 hrs, lysed neutrophils added at 0, 24, and 48 hrs (hatched bar) achieved 94% of the biofilm development seen with viable neutrophils added at 0, 24, and 48 hrs (solid bar). Both conditions resulted in significantly greater biofilm development when compared to *P. aeruginosa* in the absence of neutrophils (open bar). Plots A-D depict mean±SD of O.D. measurements (n=21). *$p<0.05$ by Dunnett's t-test.

Example 3

The following example demonstrates the enhancement of *P. aeruginosa* biofilm formation by isolated neutrophil components.

The data described in the Examples above indicates that neutrophil cellular contents are largely responsible for enhanced *P. aeruginosa* biofilm formation. Analysis of CF sputum demonstrates high concentrations of granule proteins, actin and DNA released from necrotic neutrophils (18, 28, 38). The capacity of each of these compounds to mediate enhanced early *P. aeruginosa* biofilm formation was tested. Referring to FIG. 3A, *P. aeruginosa* (▼) was combined with granule proteins (quantity equivalent to $5\times10^6$ neutrophils) compared to *P. aeruginosa* (□) in the absence of granule proteins and *P. aeruginosa* combined with live neutrophils (●). Supplementing planktonic *P. aeruginosa* with purified granule proteins failed to enhance biofilm production over a range of concentrations (FIG. 3A; Plot depicts mean±SD of O.D. crystal violet measurements (n=4). *$p<0.05$ by Student's t-test).

Neutrophil actin and DNA are also abundant in CF sputum and have been observed to bind together, forming polymers that increase the viscosity of CF sputum (38). Supplementing purified globular monomeric actin (G-actin (▲); 0.4 mg/ml) to *P. aeruginosa* under conditions known to result in formation of actin filaments (F-actin) significantly enhanced biofilm formation by 72 hrs (FIG. 3B; plot depicts mean±SEM of O.D. measurements of CV staining (n=4)).

Purified neutrophil DNA alone (X; 4 ug/ml) did not enhance *P. aeruginosa* biofilm production. However, supplementing planktonic *P. aeruginosa* with both actin and neutrophil DNA (♦) achieved an enhancement of biofilm formation, equaling 88% of the biofilm developed in the presence of live neutrophils (●) by 72 hrs. An equivalent effect on biofilm development was observed using DNA isolated from *P. aeruginosa* instead of neutrophils (data not shown); however, DNA found within CF sputa is almost entirely of human origin (28). Neutrophil lysates relatively depleted of F-actin and adjusted to an equal protein concentration as the whole cell lysates were also found to result in a significant decreased in biofilm enhancement when compared to the untreated whole cell lysates (data not shown). Addition of actin or actin with DNA to *P. aeruginosa* was significantly greater then *P. aeruginosa* alone at times 4-72 hrs (*$p<0.05$ by Dunnett's t-test).

A recent study reported that extracellular DNA (originating from *P. aeruginosa*) is required for the initial establishment of *P. aeruginosa* biofilms, and addition of DNase strongly inhibited biofilm formation (43). The addition of DNase abolished much of the neutrophil-induced enhancement of biofilm formation (FIG. 3C; plot depicts mean±S.D. of O.D. CV measurements (n=4). *$p<0.05$ by Dunnett's t-test) without significantly inhibiting bacterial growth or neutrophil survival (data not shown). The addition of gelsolin, a protein that severs noncovalent bonds between monomers of actin filaments also significantly reduced the neutrophil-induced enhancement of the biofilm, but to a much lesser extent than DNase (FIG. 3C). Although as a single component, the addition of purified actin evoked the greatest biofilm enhancement (FIG. 3C), it must be noted that detectable amounts of DNA (originating from *P. aeruginosa*) were present in the absence of added DNA or neutrophils (data not shown). Likewise, while DNase evoked the greatest reduction in biofilm enhancement (FIG. 3C), the enzyme can bind to monomeric actin and slowly depolymerize actin filaments (22).

Purified neutrophil DNA (in the absence of actin) forms small fragments with no apparent association with planktonic *P. aeruginosa* (data not shown). In the absence of exogenous DNA, actin formed filaments of varying size, and *P. aeruginosa* appeared associated with these filaments (data not shown). The combination of purified actin and DNA resulted in robust filament formation, with virtually all visible *P. aeruginosa* attached to the polymer (data not shown). The inventors devised an assay to test for binding of *P. aeruginosa* to actin. Referring to FIG. 4, planktonic *P. aeruginosa* was allowed to settle in wells coated with actin (solid bar), or BSA-blocked plastic (open bar). After 4 hours of incubation, 44% of *P. aeruginosa* was bound to F-actin, in comparison to 11% of *P. aeruginosa* which bound to G-actin, which was not different then albumin-coated plastic (FIG. 4; Plot depicts means±SD (n=3); $P<0.05$ by Student's t test).

Example 4

The following example shows *P. aeruginosa* association with actin/DNA polymers from neutrophils and in CF sputa.

Immunofluorescence of necrotic neutrophils stained for actin and DNA, revealed co-localization of both components (data not shown), and confirmed the formation of actin-DNA filaments in CF sputa, as previously reported (38). In both neutrophil lysates and CF sputa, *P. aeruginosa* localized primarily to actin-DNA filaments after 4 hours of incubation (data not shown), supporting the concept that these fibers provide a matrix for initial *P. aeruginosa* attachment and biofilm establishment. Treatment of both the neutrophil lysates and CF sputum with DNase I resulted in near complete disruption of the actin-DNA filaments and dispersion of the *P. aeruginosa*, with a greater number of visually observable planktonic bacterial cells (data not shown).

Example 5

The following example shows that, in the presence of neutrophils, *P. aeruginosa* forms multicellular aggregates.

While the present inventors have observed environmental strains of *P. aeruginosa* and PA01 do not commonly undergo autoaggregation, in CF sputum, the bacteria was found to be present only in the form of multicellular clusters. Over time, a small colony variant (SCV) phenotype can evolve in the CF airway that is associated with a high degree of autoaggregation, as well as increased virulence. When combined with neutrophils, PA01 induces rapid necrosis of the neutrophils (Walker et al., 2005, Infect Immun 73(6):3693-701), and concurrently, the bacteria is seen to form loose clusters of cells (data not shown). Although the inventors have shown that *P. aeruginosa* binds to neutrophil-derived actin and DNA to enhance biofilm growth, it is possible that this mechanism also serves to allow environmental or early CF strains to aggregate in the CF airway.

Example 6

The following example demonstrates *P. aeruginosa* response to human neutrophils is determined by *P. aeruginosa* gene expression.

Although one mechanism by which neutrophils enhance *P. aeruginosa* biofilm development is by providing a scaffolding of actin and DNA polymers, it is probable that other ligands are involved, and the receptors used by the bacteria are unknown. The inventors tested neutrophil-induced biofilm enhancement of PA01 to a number of isogenic mutant strains lacking expression of various gene products implicated in *P. aeruginosa* mediated lung disease. Significant differences in the extent of response to neutrophils were observed in the mutant strains. Deletion of the genes encoding the quorum-sensing signals rhl (ΔrhlR), las (ΔlasR) or both (ΔrhlR/lasR) resulted in little change in biofilm development in the absence of neutrophils and a significant reduction in the neutrophil-induced biofilm enhancement compared to unmodified PA01 (i.e., these mutant strains did not respond to neutrophils by developing a thicker biofilm) (FIG. 5).

PvdS is an extracytoplasmic function signal factor which is required for the production of pyoverdine, exotoxin A and PrpL protease, and functions as well to coordinate the response of the bacteria to iron starvation. Deletion of the gene pvdS has been associated with decreased biofilm development. However, deletion of the gene encoding PvdS (ΔpvdS) resulted in a robust neutrophil-induced biofilm enhancement within 4 hours, far exceeding the response of unmodified PA01 (not shown). At 72 hrs, the response of ΔpvdS equaled that of PA01 (FIG. 6). TatC is a gene that encodes for the TAT pore apparatus the regulates secretion of many proteins which determine *P. aeruginosa* virulence, as well as motility and biofilm formation (Ochsner et al., 2002, *Proc Natl Acad Sci USA* 99:8312). Deletion of tatC (ΔtatC) resulted in slightly reduced biofilm formation which was not effected by the presence of neutrophils (i.e., showed an absence of neutrophil-induced enhancement) (FIG. 6).

As previously observed, mucoid strains of *P. aeruginosa* demonstrate relatively decreased biofilm formation on abiotic surfaces. Two mucoid strains that are alginate overproducers, an isogenic mutant of PA01 with deletion of mucA (ΔmucA) and a well-characterized CF strain (FRD1) also resulted in decreased biofilms compared to unmodified PA01. However, in the presence of human neutrophils, the ability of these mutants to produce biofilms was restored, essentially nullifying the phenotypic changes induced by the genetic modification (FIG. 7). As the ability of the mutant strains to form biofilms differs, the effect of neutrophil on modifying biofilm enhancement is best appreciated when calculated as a ratio compared to bacteria alone. FIG. 8 provides an index of neutrophils-enhancement of mutant strains, where the density of the biofilm in the presence of neutrophils is plotted as a fold-increase of the biofilm density relative to the strain in the absence of neutrophils. FIG. 8 shows the fold-change evoked by neutrophils, which ranges from 1.1 for ΔrhlR/lasR to 5.1 for FRD1. Together, FIGS. 5-8 support the conclusion that the extent of *P. aeruginosa* response to human neutrophils is determined, in part, by bacterial gene expression.

Example 7

The following example demonstrates that *P. aeruginosa* binding to F-actin is determined by *P. aeruginosa* gene expression.

The inventors have devised an assay to test the ability of *P. aeruginosa* to bind to actin (see Example 3), and found significant binding of the bacteria to actin filaments (F-actin), but not to an equal quantity of purified globular monomeric actin (G-actin) following 4 hours of incubation. The inventors tested selected isogenic mutants of PA01 for differences incapacity to bind to F-actin. Considerable heterogeneity was observed in the ability of these mutants to bind F-actin (FIG. 9A; *$p<0.05$ by Dunnetts test of multiple comparisons). Of particular importance, binding of PA01 and isogenic mutants to F-actin was found to significantly correlate to the fold-change of neutrophil-induced biofilm enhancement (FIG. 9B; $R2=0.85$, $p=0.0025$). Thus, the mutant which bound F-actin to the greatest extent also had the greatest relative enhancement in biofilm development in the presence of neutrophils.

Example 8

The following example demonstrates that human neutrophils selectively modify antibiotic resistance of *P. aeruginosa* biofilms.

As human neutrophils enhance biofilm development, the inventors questioned if biofilms formed in the presence of neutrophils had altered patterns of antibiotic resistance. Biofilms and planktonic *P. aeruginosa* grown in the presence or absence of neutrophils for 24 hours were tested for susceptibility to four clinically relevant classes of antibiotics. Despite greater thickness, biofilms grown in the presence of neutrophils demonstrated significantly greater susceptibility to both tobramycin and ciprofloxacin, while susceptibility to azithromycin and ceftazidime was unchanged (Table 1). No significant changes in antibiotic susceptibilities was detected in planktonic *P. aeruginosa* in the presence of neutrophils. This selective modification of antibiotic resistance supports the conclusion that neutrophils mediate phenotypic changes in addition to greater biofilm thickness.

TABLE 1

Antibiotic susceptibility of *P. aeruginosa* strain PA01 as a planktonic population (MIC) and as a biofilm population (MBEC) as derived by the NCCLS assay

| | MIC (µg/ml) | | MBEC (µg/ml) | |
|---|---|---|---|---|
| Antibiotic | PA01 | PA01 + PMN | PA01 | PA01 + PMN |
| Azithromycin | 64 | 32 | >1024 | 1024 |
| Ceftazidime | 2 | 2 | >1024 | >1024 |
| Ciprofloxacin | 0.5 | 2 | 512 | 128 |
| Tobramycin | 1 | 0.5 | >1024 | 256 |

Example 9

The following examples shows the effects of mucin on neutrophil modification of biofilm growth.

When *P. aeruginosa* was suspended in mucin rather then RPMI media, a similar effect was observed on NUNC-TSP biofilm growth. In the absence of neutrophils, mucin increased biofilm growth, while in the presence of neutrophils no change was detected (FIG. 10; *$p<0.05$ by Student's t-test). Of even greater interest, microscopic examination of *P. aeruginosa* suspended within the mucin demonstrated the presence of small bacterial aggregates, that were markedly increased in size by the presence of neutrophils (data not shown). These aggregates of *P. aeruginosa* may represent the predominant structure of biofilms that are present in the CF airway, and the combination of neutrophils with mucin appears to enhance their formation.

Example 10

The following examples shows neutrophil-induced enhancement of Bcc biofilm growth.

Bcc represents a clinically significant infection in a subset of CF patients. The inventors questioned if neutrophils could also enhance the biofilm development of Bcc, which forms biofilms poorly in the NUNC-TSP system. In the presence of neutrophils, a selective enhancement of specific strains was observed by 24 hours (FIG. 11). Of considerable interest, some Bcc strains exhibited relatively small neutrophil enhancement, and the biofilm development of one strain (BD AU0645 strain) was inhibited in the presence of neutrophils. The tremendous heterogeneity in response to neutrophils by clinical strains of Bcc supports the conclusion that specific mechanisms regulate neutrophil-induced biofilm enhancement, and that this variability may also be present between various CF strains of *P. aeruginosa*. Although not tested in this experiment, the heterogeneity in neutrophil-induced biofilm development of Bcc could represent a portion of the variability in virulence of this organism in CF lung disease.

Example 11

The following example describes a novel model of chronic *P. aeruginosa* infection in the murine airway.

Although the agar-bead model reproduces many important features of infection in the CF airway, it is designed primarily to study the response of the lung to *P. aeruginosa*, and not the response of *P. aeruginosa* to the innate immune system. Specifically, immobilizing *P. aeruginosa* on beads or catheters bypasses mechanisms required for early biofilm formation, including interactions between bacterial adhesions and polymers originating from the host. Based on current theories of *P. aeruginosa* biofilm formation in the CF airways, and the inventors' own findings in vitro, it was believed that a number of components are required to better replicate *P. aeruginosa* biofilm formation in vivo.

1) Infection with low numbers of wild-type *P. aeruginosa*, that has not acquired virulence factors such as mucoidy. Although high concentrations of mucoid *P. aeruginosa* are eventually present in CF lung disease, the initial infection occurs with low numbers of relatively avirulent environmental strains of *P. aeruginosa* (Burns et al., 2001, *J Infect Dis* 183:444).

2) Trapping of bacteria in abnormal airway surface fluid and secretions (Boucher et al., 2002, *Adv Drug Delivery Res* 54:1359).

3) Reduced ability to clear the trapped bacteria.

4) Excessive and persistent neutrophil recruitment to the airways. The vast array of cytotoxic compounds released by activated neutrophils is clearly implicated in airway damage in CF.

5) The presence of cellular debris from necrotic neutrophils. Sputum plugs, largely comprised of necrotic neutrophils, have been identified as the location of biofilm existence in the airway, and elements of blood including RBCs, serum proteins, clotting factors, complement, platelets, are all commonly present in CF sputum.

6) Obstruction of the airway is an early and central feature in CF and is likely essential in the pathogenesis of bronchiectasis.

To achieve these features, the inventors transtracheally instilled *P. aeruginosa* ($5 \times 10^3$ of PA01) suspended in purified thrombin into a distal mouse bronchus, followed by human plasma (also containing RBCs and platelets). In the presence of plasma, thrombin induces rapid clotting of fibrinogen in situ, resulting in a focal airway plug comprised of elements present in the CF airway, and infected with low numbers of *P. aeruginosa*. Although mice subjected to this procedure demonstrated behavior consistent with an acute inflammatory insult for the first 24-48 hours, their appearance subsequently returned to baseline. Following 7 and 14 days post-infection, mice were sacrificed for analysis of infection, inflammation, and histologic changes of the lung. At day 7, *P. aeruginosa* infection in the lung (n) was below the initial inoculum, with evidence of dissemination to the spleen (c). However, by day 14, the burden of *P. aeruginosa* had increased by almost 2 logs (compared to the quantity installed at day 0), and the infection was cleared from the spleen (data not shown). Leukocyte accumulation to the airway (assessed by BAL), was robust at day 7 and persistent at day 14, while animals receiving plasma and thrombin in the absence of bacteria returned to baseline levels (data not shown). Lung histology (by H&E staining) demonstrated intense areas of focal lung inflammation (data not shown), with scattered clusters of "WBC clots" within the airways (data not shown). These airway plugs may represent a site of persistent infection, based on findings from the CF lung. However, microcolonies of *P. aeruginosa*, or classic features of bronchiectasis, were not apparent at 14 days.

Each publication cited herein is incorporated herein by reference in its entirety.

REFERENCES

1. Aaron et al., 2002, J Clin Microbiol 40:4172-4179.
2. Balfour-Lynn, 1999, J R Soc Med 92 Suppl 37:23-30.
3. Borregaard and Cowland, 1997, Blood 89:3503-3521.
4. Brinkmann et al., 2004, Science 303:1532-1535.
5. Britigan and Edeker. 1991, J Clin Invest 88:1092-1102.
6. Burns et al., 2001, J Infect Dis 183:444-452.
7. Dakin et al., 2002, Am J Respir Crit Care Med 165:904-910.
8. Darouiche, 2001, Clin Infect Dis 33:1567-1572.
9. Deziel et al., 2001, J Bacteriol 183:1195-1204.
10. Downey et al., 1993, Am Rev Respir Dis 147:168-176.
11. Drenkard et al., 2002, Nature 416:740-743.
12. Edwards et al., 2003, Regulation of Neutrophil Apoptosis, p. 204-224. In M. A. Cassatella (ed.), The Neutrophil, vol. 83. Karger.
13. Emerson et al., 2002, Pediatr Pulmonol 34:91-100.
14. Ernst et al., 1999, Science 286:1561-1565.
15. Favre-Bonte and C. Van Delden, 2003. J Antimicrob Chemother 52:598-604.
16. CF Foundation. 2004. CF Foundation: Patient Registry 2003 Annual Data Report. CF Foundation.
17. Frederiksen et al., 1996, Pediatr Pulmonol 21:153-158.
18. Goldstein and Doring, 1986, Am Rev Respir Dis 134:49-56.
19. Gong et al., 2000, J Biol Chem 275:8970-8974.
20. Hammer et al., 1981, J Lab Clin Med 98:938.
21. Haslett et al., 1985, Am J Pathol 119:101-110.
22. Hitchcock et al., 1976, Cell 7:531-542.
23. Hook and Sande, 1974, Infect Immun 10:1433-1438.
24. Justice et al., 2004, PNAS 101:1333-1338.
25. Khan et al., 1995, Am J Respir Crit Care Med 151:1075-1082.
26. Klausen et al., 2003, Mol Microbiol 48:1511-1524.
27. Lee et al., 1993, J Leukocyte Biology 54:283-288.
28. Lethem et al., 1990, Eur Respir J 3:19-23.
29. Muhlebach et al., 2002, Am J Respir Crit Care Med 165:911-915.
30. Muhlebach et al., 1999, Am J Respir Crit Care Med 160:186-191.
31. Ochsner et al., 2002, Proc Natl Acad Sci USA 99:8312-8317.
32. Parad et al., 1999, Infect Immun 67:4744-4750.
33. Perks et al., 2000, Am J Respir Crit Care Med 162:1767-1772.
34. Riches et al., 1990, J Immunol 145:3062-3070.
35. Rosenfeld et al., 2001, Pediatr Pulmonol 32:356-366.
36. Roum et al., 1993, J Appl Physiol 75:2419-2424.
37. Schaedel et al., 2002, Pediatr Pulmonol 33:483-491.
38. Sheils et al., 1996, Am J Pathol 148:919-927.
39. Singh et al., 2002, Nature 417:552-555.

40. Singh et al., 2000, Nature 407:762-764.
41. Spencer et al., 2003, J Bacteriol 185:1316-1325.
42. Vasconcellos et al., 1994, Science 263:969-971.
43. Whitchurch et al., 2002, Science 295:1487.
44. Wilderman et al., 2001, Infect Immun 69:5385-5394.
45. Worlitzsch et al., 2002, J Clin Invest 109:317-325.
46. Yoon et al., 2002, Dev Cell 3:593-603.

While various embodiments of the present invention have been described in detail herein, it is apparent that modifications and adaptations of those embodiments will occur to those skilled in the art. It is to be expressly understood, however, that such modifications and adaptations are within the scope of the present invention, as set forth in the following claims:

What is claimed is:

1. A method to reduce biofilms in a subject diagnosed as having biofilms, the biofilms forming as a result of the contact of the subject with a medical device, a graft, a catheter, a stent, a wound dressing, or a prosthesis; being associated with the presence of necrotic cells; and being produced by a microorganism that has enhanced biofilm formation in the presence of said necrotic cells, the method comprising administering to a subject that has biofilms, a compound that inhibits the formation or polymerization of actin microfilaments or depolymerizes actin microfilaments at or proximal to the site of biofilm formation or the site of infection by said microorganism wherein inhibition of the formation or polymerization of actin microfilaments or the depolymerization of actin filaments reduces biofilms in the subject, wherein the compound is selected from the group consisting of latrunculins and swinholides.

2. The method of claim 1, wherein the actin microfilaments are formed from the content of said necrotic cell that undergoes necrosis at or proximal to the site of biofilm formation or the site of infection by said microorganism that forms biofilms.

3. The method of claim 2, wherein the necrotic cell is a neutrophil.

4. The method of claim 1, further comprising administering to the subject an anti-DNA compound.

5. The method of claim 1, further comprising administering to the subject an anti-mucin compound.

6. The method of claim 1, further comprising administering to the subject a compound for treatment of a disease or condition associated with said biofilm formation.

7. The method of claim 1, wherein the compound is administered with a pharmaceutically acceptable carrier.

8. The method of claim 1, wherein the compound is administered directly to or proximal to the site of said biofilm formation or the site of infection by a microorganism that forms biofilms.

9. The method of claim 1, wherein the compound is administered to the lung or airways of the subject.

10. The method of claim 1, wherein the compound is applied to a prosthetic graft or administered to the subject receiving the graft prior to or during the implantation or utilization of the graft.

11. The method of claim 1, wherein the compound is applied to a catheter prior to or during use of the catheter by a subject.

12. The method of claim 1, wherein the compound is applied to the site of a wound or to the wound dressing when the wound is treated.

13. The method of claim 1, wherein the compound is applied to a medical device that contacts a subject tissue surface during use of the medical device by a subject.

14. The method of claim 1, wherein the biofilm forms in connection with a disease or condition in an organ, tissue or body system.

15. The method of claim 1, wherein the biofilm forms on a surface of a tissue, organ or bodily part proximal to or at the site of the application of the medical device, graft, catheter, stent, wound dressing, or prosthesis.

16. The method of claim 1, wherein the biofilm forms in connection with a condition selected from the group consisting of: catheter-related infection (kidney, vascular, peritoneal), medical device-related infections, orthopedic implant infection, wounds, and biliary stents, wherein the condition is associated with the presence of necrotic cells at the site of biofilm formation.

17. The method of claim 1, wherein the microorganism is *Pseudomonas aeruginosa*.

18. The method of claim 1, wherein the microorganism is a bacterium.

19. The method of claim 1, wherein the microorganism is *Burkholderia*.

20. A method to reduce biofilms in a subject diagnosed as having biofilms, the biofilms forming as a result of the contact of the subject with a medical device, a graft, a catheter, a stent, a wound dressing, or a prosthesis, and being associated with the presence of necrotic cells; the biofilms being produced by a microorganism that has enhanced biofilm formation in the presence of said necrotic cells, the method comprising administering to a subject that has said biofilms: (1) a first compound that inhibits the formation or polymerization of actin microfilaments or depolymerizes actin microfilaments, wherein the first compound is selected from the group consisting of latrunculins, and swinholides; and (2) an anti-DNA compound, wherein the first compound and the anti-DNA compound are administered at or proximal to the site of said biofilm formation or the site of infection by said microorganism, wherein inhibition of the formation or polymerization of actin microfilaments or the depolymerization of actin filaments and the administration of the anti-DNA compound, reduces biofilms in the subject.

* * * * *